US006558663B1

(12) United States Patent
Seebach et al.

(10) Patent No.: US 6,558,663 B1
(45) Date of Patent: May 6, 2003

(54) TRANSGENIC SWINE & SWINE CELLS HAVING HUMAN HLA GENES

(75) Inventors: Joerg Seebach, Boston, MA (US); David H. Sachs, Newton, MA (US); Harout DerSimonian, Wellesley, MA (US); Christian LeGuern, Newton, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/457,177

(22) Filed: Dec. 8, 1999

Related U.S. Application Data

(62) Division of application No. 08/692,843, filed on Aug. 2, 1996, now Pat. No. 6,030,833.
(60) Provisional application No. 60/001,900, filed on Aug. 4, 1995.

(51) Int. Cl.[7] .......................... A61K 48/00; C12N 5/02; C12N 15/00; A01K 67/033

(52) U.S. Cl. ................... 424/93.21; 424/93.2; 435/325; 435/320.1; 800/8; 800/13; 800/17; 800/21

(58) Field of Search .................. 424/93.2, 93.21; 435/325, 320.1; 800/8, 13, 17, 21

(56) References Cited

U.S. PATENT DOCUMENTS

| 5,416,260 A | | 5/1995 | Koller et al. ............... 800/11 |
| 5,596,087 A | | 1/1997 | Silversides et al. ........ 536/24.3 |
| 5,614,187 A | * | 3/1997 | Sachs ...................... 424/93.21 |
| 6,030,833 A | * | 2/2000 | Seebach et al. ............ 435/325 |

FOREIGN PATENT DOCUMENTS

| WO | WO 91/05855 | 5/1991 |
| WO | WO 93/02188 | 2/1993 |
| WO | WO 93/09815 | 5/1993 |
| WO | WO 94/26289 | 11/1994 |
| WO | WO 96/01120 | 1/1996 |
| WO | WO 96/06165 | 2/1996 |

OTHER PUBLICATIONS

Sachs; Transplantation Tolerance, 1993, CCCETS Basic Science Lecture; Ann Thorac Surg56: 1221–1227.*
Sablinski et. al.; Pig to monkey bone marrow and kidney xenotransplantation, 1997, Surgery: 381–391.*
Shimizu, Y. et al., Eur. J. Immunol. 19:447–451
Bodmer, JG et al., Tissue Antigens. 44:1–18.
Allavena et al., "Molecules and Structures Involved in the Adhesion of Natural Killer Cells to Vascular Endothelium," J. Exp. Med. 173:439–448 (1991).
Bach et al., "Delayed Xenograft Rejection," Immunol. Today, 17:379–384 (1996).
Bennett et al., "Hybrid Resistance: Negative and Positive Signaling of Murine Natural Killer Cells," Semin. Immunol., 7:121–127 (1995).
Correa et al., "Multiple Natural Killer Cell–Activating Signals are inhibited by Major Histocompatibility Complex . . ." Eur. J. Immunol. 24:1323–1331 (1994).
Goodman et al., "Direct Activation of Porcine Endothelial Cells by Human Natural Killer Cells," Transplantation, 61:763–771 (1996).
Gumperz et al., "The Enigma of the Natural Killer Cell," Nature, 378:245–248 (1995).
Inverardi et al., "Early Events in Cell–Mediated Recognition of Vascularized Xenografts," Immunol. Rev. 141:71–93 (1994).
Karre, "Express Yourself or Die: Peptides, MHC Molecules, and NK Cells," Science 267:978–979 (1995).
Kaufman et al., "Xenotransplantation," Annu. Rev. Immunologyn. 13:339–367 (1995).
Kirk et al., "Ex Vivo Characterization of Human Anti–Porcine Hyperacute Cardiac Rejection," Transplantation 56:785–793 (1993).
Kirk et al., "The Human Antiporcine Cellular Repertoire . . ." Transplantation, 55:924–931 (1993).
Lanier et al., "Inhibitory MHC Class I receptors on NK Cells and T Cells," Immunology Today, 17:86–91 (1996).
Lanier et al., "The NKB1 and HP–3E4 NK Cells Receptors are Structurally Distinct Glycoproteins and Independently Recognize . . ." J. Immunol. 154:3320–3327 (1995).
Lanier et al., "The Role of Natural Killer Cells in Transplantation," Curr. Opin. Immunol. 7:626–631 (1995).
Lowdell et al., "VLA–6 (CDw49f) is an Important Adhesion Molecule in NK Cell–Mediated Cytotoxicity . . ." Exp. Hematol. 23: 1530–1534 (1995).
Madden, "The Three–Dimensional Structure of Peptide–MHC Complexes," Annu. Rev. Immunol. 13:587–622 (1995).
Malnati et al., "Peptide Specificity in the Recognition of MHC Class I by Natural Killer Cells Clones," Science, 267:1016–1018 (1995).
Moretta et al., "Receptors for HLA Class–1 Molecules in Human Natural Killer Cells," Annu. Rev. Immunol. 14:619–648 (1996).
Pazmany et al., "Protection From Natural Killer Cell Mediated Lysis by HLA–G Expression on Target Cells," Science 274:792–795 (1996).
Wagtmann et al., "Killer Cell Inhibitory Receptors Specific for HLA–C and HLA–B . . ." Immunity, 3:801–809 (1995).
Wagtmann et al., "Molecular Clones of the p58 NK Cell Receptor Reveal . . ." Immunity, 2:439–449 (1995).
Watkins, "The Evolution of Major Histocompatibility Class I Genes in Primates," Crit. Rev. Immunol. 15:1–29 (1995).
Clark et al., "The Human Hematopoietic Colony–Stimulating Factors," Science 236: 1229–1237 (1987).

(List continued on next page.)

Primary Examiner—Anne M. Wehbe'
(74) Attorney, Agent, or Firm—Fish & Richardson P.C.

(57) ABSTRACT

Methods of promoting tolerance and inhibiting NK cell mediated attack in a human recipient to a swine graft are disclosed The methods include introducing into the recipient a swine hematopoietic stem cell which has been transformed with a transgene encoding a human MHC class I protein that inhibits recipient NK cell mediated attack.

16 Claims, 1 Drawing Sheet

OTHER PUBLICATIONS

Figure 1A:
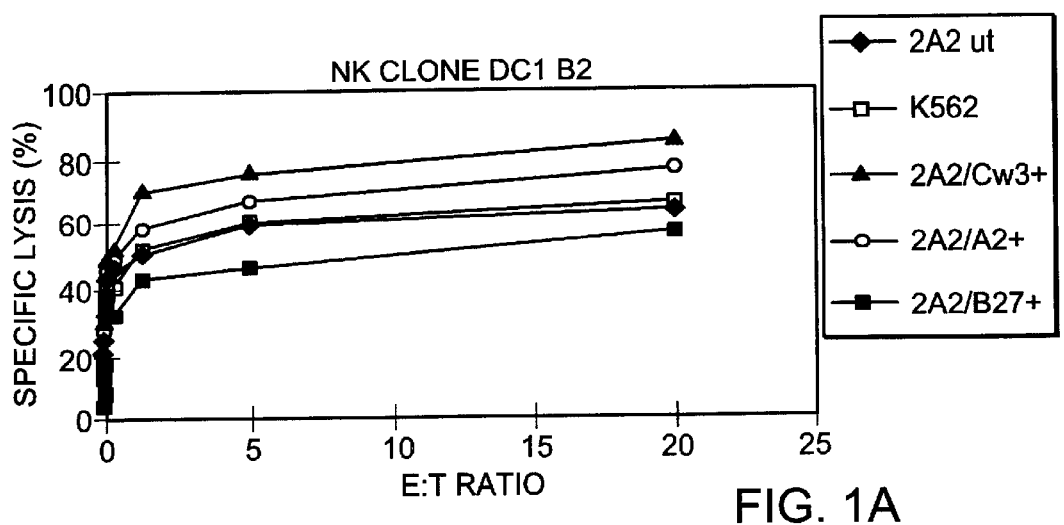

Emery et al., "Retrovirus–mediated Transfer and Expression . . ." Blood 81 (9): 2460–2465 (1993).

Foxwell et al., "Cytokine Receptors: Structure and Signal Transduction," Clin. Exp. Immunol. 90: 161–169 (1992).

Hagihara et al., "Porcine Histocompatibility Matching Test Using HLA . . ." Transpl. Proc. 26(4): 1869 (1994).

Nabel et al., "Transduction of a Foreign Histocompatibility Gene . . ." PNAS 89: 5157–5161 (1992).

Sakamaki et al., "Critical Cytoplasmic Domains of the Common β subunit . . ." EMBO Journal 11: 3541–3549 (1992).

Shimada et al., "A Single Retroviral Vector for Transfer of Multiple Major . . ." Transpl. Proc. 27(1): 180–181 (1995).

Tsuji et al., "The Role of HLA Class II Antigens/Genes in Xenogeneic Iso, Allo and Xenotransplantation," Transpl. Proc. 26(4):2441–2443 (1994).

Velander et al., "High–level Expression of a Heterologous Protein in the Milk of Transgenic Swine . . ." PNAS 89:12003–12007 (1992).

Rao et al., "Recombinant Hemoglobin A Produced in Transgenic Swine. . ." Art. Cells, Blood Subs., and Immob. Biotech., 22(3), 695–700 (1994).

Cozzi et al., "Expression of Human Decay Accelerating Factor . . ." Transpl. Proc. 26: 1402–1403 (1994).

Katz et al., "Structure Determination of Aquomet Porcine . . ." J. Mol. Biol. 144:541–553 (1994).

Fodor et al. (1994), "Expression of a functional human complement inhibitor in a transgenic pig as a model for the prevention of xenogeneic hyperacute organ rejection," Proc. Natl. Acad. Sci. U S A. 91(23):11153–7.

O'Donnell et al. (1994), "Influence of the chemical nature of side chain at beta 108 of hemoglobin A on the modulation of the oxygen affinity by chloride ions. Low Oxygen affinity variants of human hemoglobin expressed in transgenic pigs: hemoglobins Presbyterian and Yoshizuka," J. Biol. Chem. 269(44):27692–9.

Pinkert et al. (1994), "Liver, renal and subcutaneous histopathology in PEPCK–bGH transgenic pigs," Transgenic Res. 3(6):401–5.

Langford et al. (1994), "Production of pigs transgenic for human decay accelerating factor," Transplant Proc. 26(3):1400–1.

Morcol et al. (1994), "The porcine mammary gland as a bioreactor for complex proteins," Ann. NY Acad. Sci. 721:218–33.

Solomon et al. (1994), "Lipid composition of carcass tissue from transgenic pigs expressing a bovine growth hormone gene," J. Anim. Sci. 72(5):1242–6.

Logan et al. (1994), "Transgenic swine as a recombinant production system for human hemoglobin," Methods Enzymol. 231:435–45.

Sharma et al. (1994), "An isologous porcine promoter permits high level expression of human hemoglobin in transgenic swine," Biotechnology 12(1):55–9.

Kaufman et al. Annu. Rev. Immunol. 13: 339–67, Jul. 1995.*

Mullins et al. J. Clin. Invest. 98(11):S37–39, 1996.*

Palmiter et al. Ann. Rev. Genet. 20:465–99, 1986.*

Shimizu et al. Eur. J. Immunol. 19: 447–451, 1989.*

* cited by examiner

TRANSGENIC SWINE & SWINE CELLS HAVING HUMAN HLA GENES

This patent application is a divisional of U.S. patent application Ser. No. 08/692,843, filed Aug. 2, 1996 (which issued as U.S. Pat. No. 6,030,833 on Feb. 29, 2000), which claims priority to U.S. Provisional Application No. 60/001,900, filed Aug. 4, 1995, the contents of which are hereby incorporated by reference.

BACKGROUND OF THE INVENTION

The invention relates to the field of organ transplantation.

Technical advances in allogeneic organ transplantation and the availability of nonspecific immunosuppressive agents have revolutionized the field of organ transplantation. This progress has, however, resulted in a shortage of essential organs of suitable size and match.

The shortage of allograft-organs has led to an increased interest in xenogeneic transplantation. It was demonstrated more than twenty-five years ago that transplants from chimpanzee to man could provide long-term life-supporting function. However, the use of non-human primates as an organ source is of limited applicability. Many primate species are scarce and protected, and those that are more plentiful, such as the baboon, often do not grow to a size which allows the use of their organs in adults. Moreover, in some cultures, the use of primates as a source of organs is ethically unacceptable.

Some of these difficulties could be resolved by use of ungulate organs, especially pig organs. Pigs are domesticated, easy to breed, have large litters, and grow rapidly to the size which allow the use of their organs in the very largest human beings. In addition, pig and man have many anatomical and physiological similarities. However, transplantation of a pig organ into a human results in a vigorous rejection of the graft-organ.

SUMMARY OF THE INVENTION

In general, the invention features, a genetically engineered swine cell, e.g., a cultured swine cell, a retrovirally transformed swine cell, or a cell derived from a transgenic swine. The cell includes a transgene which encodes a xenogeneic, e.g., a human, class I MHC protein, e.g., an HLA A, B, C or G gene.

In preferred embodiments the transgene includes an α subunit, e.g., an HLA class I gene, e.g., an HLA C gene.

Where the transgene includes an HLA C gene, the allele, by way of example, can be any Cw1, Cw2, Cw3, Cw4, Cw5, Cw6, Cw7, Cw8, Cw9, Cw7/8v, or Cw10 allele. As is discussed below, alleles of HLA class I genes can often be classed into reactivity groups wherein an allele from a reactivity group can confer protection against NK cells specific to other alleles in the reactivity group. Thus, in preferred embodiments, the transgene includes an allele which is a member of a reactivity group, e.g., a Group 1 allele, e.g., any of an HLA C Cw2, Cw4, Cw5, or Cw6 allele, or a Group 2 allele, e.g., any of an HLA C Cw1, Cw3, Cw7, or Cw8 allele. In other preferred embodiments the allele has: an Asn at residue 77 and a Lys at residue 80; or a Ser at residue 77 and an Asn at residue 80.

In preferred embodiments the transgene includes an HLA A gene. In other preferred embodiments the transgene includes an HLA B gene.

In other preferred embodiments the transgene includes an HLA G gene, e.g, any of alleles I–IV of HLA G.

In preferred embodiments: the cell includes a second transgene which includes a class I MHC protein. In preferred embodiments the second transgene includes an HLA class I gene, e.g., an HLA A, B, C or G gene. In preferred embodiments the first transgene includes an allele from a first reactivity group and the second transgene includes an allele from a second reactivity group. For example, the first transgene includes a Group 1 allele, e.g., any of an HLA C Cw2, Cw4, Cw5, or Cw6 allele, and the second transgene includes a Group 2 allele, e.g., any of an HLA C Cw1, Cw3, Cw7, or Cw8 allele. In preferred embodiments the first transgene encodes an allele which has an Asn at residue 77 and a Lys at residue 80 and the second transgene encodes an allele which has a Ser at residue 77 and an Asn at residue 80. In other preferred embodiments the second transgene encodes a human β subunit, e.g., a β-2 microglobulin gene.

In preferred embodiments the transgene includes a chimeric class I gene, e.g., a chimeric HLA A, B, C, or G gene. The chimeric transgene can include a first portion derived from a first allele of a gene encoding a class I protein and a second portion derived from a second allele of the gene encoding the class I protein. In other embodiments, the class I gene is a synthetic sequence selected for the ability to produce a protein which protects a target cell from attack from more than one class of NK cells. In preferred embodiments the transgene includes a gene, e.g., a chimeric or mutated HLA C gene, which confers protection to more than one class of NK cells, e.g., an allele of HLA C having serine at position 77 and lysine at position 80, see e.g., Biassoni, 1995, J. Exp. Med. Vol. 182: 605–609, hereby incorporated by reference. See also Moretta et al., 1996, Ann. Rev. Immunol. 14: 619–648, hereby incorporated by reference, which together with the disclosure herein, provides guidance for altering critical residues in the HLA C genes.

In yet other preferred embodiments the genetically engineered swine cell is: a swine hematopoietic stem cell, e.g., a cord blood hematopoietic stem cell, a bone marrow hematopoietic stem cell, or a fetal or neonatal liver or spleen hematopoietic stem cell; derived from differentiated blood cells, e.g. a myeloid cell, such as a megakaryocyte, monocyte, granulocyte, or an eosinophil; an erythroid cell, such as a red blood cell, e.g. a lymphoid cell, such as B lymphocytes and T lymphocytes; derived from a pluripotent hematopoietic stem cell, e.g. a hematopoietic precursor, e.g. a burst-forming units-erythroid (BFU-E), a colony forming unit-erythroid (CFU-E), a colony forming unit-megakaryocyte (CFU-Meg), a colony forming unit-granulocyte-monocyte (CFU-GM), a colony forming unit-eosinophil (CFU-Eo), or a colony forming unit-granulocyte-erythrocyte-megakaryocyte-monocyte (CFU-GEMM); a swine cell other than a hematopoietic stem cell, or other blood cell; a swine thymic cell, e.g., a swine thymic stromal cell; a bone marrow stromal cell; a swine liver cell; a swine kidney cell; a swine epithelial cell; a swine hematopoietic progenitor cell; a swine muscle cell, e.g., a heart cell; an endothelial cell; or a dendritic cell or precursor thereof.

In yet other preferred embodiments the cell is: isolated or derived from cultured cells, e.g., a primary culture, e.g., a primary cell culture of hematopoietic stem cells; isolated or derived from a transgenic animal.

In yet other preferred embodiments: the swine cell is homozygous for the transgene; the swine cell is heterozygous for the transgene; the swine cell is homozygous for the transgene (heterozygous transgenic swine can be bred to produce offspring that are homozygous for the transgene); the swine cell includes two or more transgenes.

In yet other preferred embodiments the cell includes a one or more, or all of, of a transgene which encodes an HLA A gene, a transgene which encodes an HLA B gene, a transgene which encodes an HLA C gene, and a transgene which encodes an HLA G gene.

In another aspect, the invention features a nucleic acid, e.g., a transgene, including a swine promoter operably linked to a xenogeneic, e.g., human, nucleic acid which encodes a class I MHC protein. The swine promoter can be, e.g., a swine hematopoietic epithelial gene promoter, or a heterologous inducible or developmentally regulated promoter.

In preferred embodiments the nucleic acid includes, e.g., a gene which encodes an α subunit, e.g., an HLA class I gene, e.g., an HLA A, B, C, or G gene, or a gene which encodes a human β subunit, e.g., a β-2 microglobulin gene Where the nucleic acid includes an HLA C gene, the allele, by way of example, can be any Cw1, Cw2, Cw3, Cw4, Cw5, Cw6, Cw7, Cw8, Cw9, Cw7/8v, or Cw10 allele. In preferred embodiments the nucleic acid encodes an allele which is a member of a reactivity group, e.g., a Group 1 allele, e.g., any of an HLA C Cw2, Cw4, Cw5, or Cw6 allele, or a Group 2 allele, e.g., any of an HLA C Cw1, Cw3, Cw7, or Cw8 allele. In other preferred embodiments the allele has an Asn at residue 77 and a Lys at residue 80 or a Ser at residue 77 and an Asn at residue 80.

In preferred embodiments, the nucleic acid or transgene further includes transcriptional regulatory sequences, e.g. a tissue-specific promoter, e.g., a hematopoietic specific promoter, operably linked to the non-swine gene sequence.

In preferred embodiments the nucleic acid or transgene encodes a chimeric class I protein, e.g., a chimeric HLA A, B, C, or G protein. The chimeric transgene can include a first portion derived from a first allele of a gene encoding a class I protein and a second portion derived from a second allele of the gene encoding the class I protein. In other embodiments, the class I gene is a synthetic sequence selected for the ability to produce a protein which protects a target cell from attack from more than one class of NK cells. In preferred embodiments the transgene is a chimeric or mutated HLA C gene which confers protection to more than one class of NK cells, e.g., an allele of HLA C having serine at position 77 and lysine at position 80.

In another aspect, the invention features, a transgenic swine having cells which include a xenogeneic, e.g., a human, nucleic acid, e.g., a transgene which encodes an HLA class I protein. In preferred embodiments the transgene can include a nucleic acid which encodes an α subunit, e.g., an HLA class I gene, e.g., one or more of. In other preferred embodiments the transgene includes a nucleic acid which encodes a human β subunit, e.g. β-2 microglobulin gene.

In preferred embodiments in which the transgene includes an HLA C gene, the allele, by way of example, can be any Cw1, Cw2, Cw3, Cw4, Cw5, Cw6, Cw7, Cw8, Cw9, Cw7/8v, or Cw10 allele. In preferred embodiments the transgene includes an allele which is a member of a reactivity group, e.g., a Group 1 allele, e.g., any of an HLA C Cw2, Cw4, Cw5, or Cw6 allele, or a Group 2 allele, e.g., any of an HLA C Cw1, Cw3, Cw7, or Cw8 allele. In other preferred embodiments the allele has an Asn at residue 77 and a Lys at residue 80 or a Ser at residue 77 and an Asn at residue 80.

In preferred embodiments the transgene encodes a chimeric class I protein, e.g., chimeric HLA A, B, C, or G gene. The chimeric transgene can include a first portion derived from a first allele of a gene encoding a class I protein and a second portion derived from a second allele of the gene encoding the class I protein. In other embodiments, the class I gene is a synthetic sequence selected for the ability to produce a protein which protects a target cell from attack from more than one class of NK cells. In preferred embodiments the transgene includes a gene, e.g., a chimeric or mutated HLA C gene, which confers protection to more than one class of NK cells, e.g., an allele of HLA C having serine at position 77 and lysine at position 80.

In preferred embodiments: the transgenic swine includes a second transgene which encodes a class I MHC protein. In preferred embodiments the transgene includes a gene which encodes a human β subunit, e.g., a β-2 microglobulin gene. In other preferred embodiments the second transgene includes an HLA class I gene, e.g., an HLA A, B, C, or G gene. In preferred embodiments the first transgene includes an allele from a first reactivity group and the second transgene includes an allele from a second reactivity group. In preferred embodiments the transgene includes an allele which is a member of a reactivity group, e.g., a Group 1 allele, e.g., any of an HLA C Cw2, Cw4, Cw5, or Cw6 allele, or a Group 2 allele, e.g., any of an HLA C Cw1, Cw3, Cw7, or Cw8 allele. In other preferred embodiments the first transgene encodes an HLA C allele which has an Asn at residue 77 and a Lys at residue 80 and the second transgene encodes an HLA C allele which has a Ser at residue 77 and an Asn at residue 80.

In yet other preferred embodiments: the transgenic swine cell is hemizygous for the transgene; the transgenic swine cell is hemizygous for the transgene; the transgenic swine is heterozygous for the transgene; the transgenic swine is homozygous for the transgene (heterozygous transgenic swine can be bred to produce offspring that are homozygous for the transgene); the transgenic swine includes two or more transgenes.

In yet other preferred embodiments the transgenic swine includes a one or more, or all, of a transgene which encodes an HLA A gene, a transgene which encodes an HLA B gene, a transgene which encodes an HLA C gene, a transgene which encodes an HLA G gene.

Transgenic swine (or swine cells) of the invention can be used as a source for "humanized" tissue for grafting into a human recipient, e.g., hematopoietic cells or other tissues or organs.

In another aspect, the invention features, a swine organ or a swine tissue, having cells which include a xenogeneic, e.g., a human, nucleic acid, e.g., a transgene which encodes an HLA class I protein. In preferred embodiments the transgene can include a nucleic acid which encodes an α subunit, e.g., an HLA class I gene, e.g., an HLA A, B, C, or G gene. In other preferred embodiments the transgene includes a nucleic acid which encodes a human β subunit, e.g. β-2 microglobulin gene.

In preferred embodiments the organ is a heart, lung, kidney, pancreas, or liver.

In preferred embodiments the tissue is: thymic tissue; islet cells or islets; stem cells; bone marrow; endothelial cells; skin; or vascular tissue.

In preferred embodiments in which the transgene includes an HLA C gene, the allele, by way of example, can be any Cw1, Cw2, Cw3, Cw4, Cw5, Cw6, Cw7, Cw8, Cw9, Cw7/8v, or Cw10 allele. In preferred embodiments the transgene includes an allele which is a member of a reactivity group, e.g., a Group 1 allele, e.g., any of an HLA C Cw2, Cw4, Cw5, or Cw6 allele, or a Group 2 allele, e.g., any of an HLA C Cw1, Cw3, Cw7, or Cw8 allele. In other preferred embodiments the allele has an Asn at residue 77 and a Lys at residue 80 or a Ser at residue 77 and an Asn at residue 80.

In preferred embodiments the transgene encodes a chimeric class I protein, e.g., chimeric HLA A, B, C, or G gene. The chimeric transgene can include a first portion derived from a first allele of a gene encoding a class I protein and a second portion derived from a second allele of the gene encoding the class I protein. In other embodiments, the class I gene is a synthetic sequence selected for the ability to produce a protein which protects a target cell from attack from more than one class of NK cells. In preferred embodiments the transgene includes a gene, e.g., a chimeric or mutated HLA C gene, which confers protection to more than one class of NK cells, e.g., an allele of HLA C having serine at position 77 and lysine at position 80.

In yet other preferred embodiments: the transgenic swine organ or tissue includes: a cell which is hemizygous for the transgene; a cell which is hemizygous for the transgene; a cell which is heterozygous for the transgene; a cell which is homozygous for the transgene (heterozygous transgenic swine can be bred to produce offspring that are homozygous for the transgene); a cell which includes two or more transgenes.

In preferred embodiments: the swine organ or tissue includes cells which include a second transgene which encodes a class I MHC protein. In preferred embodiments the second transgene includes a gene which encodes a human β subunit, e.g., a β-2 microglobulin gene. In other preferred embodiments the second transgene includes an HLA class I gene, e.g., an HLA A, B, C, or G gene. In preferred embodiments the first transgene includes an allele from a first reactivity group and the second transgene includes an allele from a second reactivity group. In preferred embodiments the first transgene includes an allele which is a member of a reactivity group, e.g., a Group 1 allele, e.g., any of an HLA C Cw2, Cw4, Cw5, or Cw6 allele, and the second transgene includes a Group 2 allele, e.g., any of an HLA C Cw1, Cw3, Cw7, or Cw8 allele. In other preferred embodiments the first transgene includes an allele which has an Asn at residue 77 and a Lys at residue 80 and the second transgene includes an allele which has a Ser at residue 77 and an Asn at residue 80.

In yet other preferred embodiments the organ or tissue includes one or more, or all, of a transgene which encodes an HLA A gene, a transgene which encodes an HLA B gene, a transgene which encodes an HLA C gene, a transgene which encodes an HLA G gene.

The swine organs and tissues of the invention can be used as a source for "humanized" tissue for grafting into a human recipient, e.g., hematopoietic cells or other tissues or organs.

Graft tissue which expresses a recipient species-MHC class I gene can be used to improve methods of transplanting xenogeneic tissue into a recipient. For example, acceptance of porcine tissue by a human recipient can be prolonged if the porcine tissue expresses a human class I gene, preferably the HLA C gene. The use of graft tissue which expresses an HLA class I gene can be combined with methods of inducing tolerance described herein.

Accordingly, in another aspect, the invention features a method of inducing tolerance in a recipient mammal, e.g., a primate, e.g., a human, to a graft from a swine, e.g., a miniature swine. The method includes:

inserting DNA encoding a swine MHC antigen, preferably a class I antigen, a class II antigen, or both, into a hematopoietic stem cell, e.g., a bone marrow hematopoietic stem cell, of the recipient mammal;

allowing the MHC antigen encoding DNA to be expressed in the recipient; and implanting the graft in the recipient, wherein some or substantially all of the cells of the graft express a recipient species class I gene which inhibits recipient NK cell mediated attack.

In preferred embodiments the graft tissue expresses an HLA C gene. The allele, by way of example, can be any Cw1, Cw2, Cw3, Cw4, Cw5, Cw6, Cw7, Cw8, Cw9, Cw7/8v, or Cw10 allele. In preferred embodiments the allele is a member of a reactivity group, e.g., a Group 1 allele, e.g., any of an HLA C Cw2, Cw4, Cw5, or Cw6 allele, or a Group 2 allele, e.g., any of an HLA C Cw1, Cw3, Cw7, or Cw8 allele. In other preferred embodiments the allele has an Asn at residue 77 and a Lys at residue 80 or a Ser at residue 77 and an Asn at residue 80.

In preferred embodiments the graft expresses an HLA A gene. In other preferred embodiments the graft expresses an HLA B gene. In other preferred embodiments the graft expresses an HLA G gene, e.g, any of alleles I–IV of HLA G. In yet other preferred embodiments the graft includes one or more, or all, of a transgene which encodes an HLA A gene, a transgene which encodes an HLA B gene, a transgene which encodes an HLA C gene, a transgene which encodes an HLA G gene.

In preferred embodiments: the graft includes a first transgene which includes an HLA class I allele, e.g., an HLA C allele, and a second transgene which includes a gene which encodes a class I MHC protein. In preferred embodiments the second transgene includes a human β subunit, e.g., a β-2 microglobulin gene. In other preferred embodiments the first transgene includes an HLA class I allele from a first reactivity group and the second transgene includes an allele from the second reactivity group. For example, the first transgene includes a Group 1 allele, e.g., any of an HLA C Cw2, Cw4, Cw5, or Cw6 allele, and the second transgene includes a Group 2 allele, e.g., any of an HLA C Cw1, Cw3, Cw7, or Cw8 allele. In preferred embodiments the first transgene encodes an allele which has an Asn at residue 77 and a Lys at residue 80 and the second transgene encodes an allele which has a Ser at residue 77 and an Asn at residue 80. In other preferred embodiments the second transgene encodes a human β subunit, e.g., a β-2 microglobulin gene.

In preferred embodiments the graft expresses a chimeric class I protein, e.g., chimeric HLA A, B, C, or G gene. For example, the chimeric gene includes a first portion derived from a first allele of the gene encoding the class I protein and a second portion derived from a second allele of the gene encoding the class I protein. In other embodiments, the class I gene is a synthetic sequence selected for the ability to produce a protein which protects a target cell from attack from more than one class of NK cells. In preferred embodiments the transgene includes a gene, e.g., a chimeric or mutated HLA C gene, which confers protection to more than one class of NK cells, e.g., an allele of HLA C having serine at position 77 and lysine at position 80.

In preferred embodiments the graft is from a transgenic swine, e.g., a transgenic swine which includes a transgenic human class I gene, e.g., an HLA A, B, C, or G gene.

In preferred embodiment, the method further includes: administering to the recipient a short course of help reducing treatment, e.g., a short course of high dose cyclosporine treatment. The short course of help reducing treatment is generally administered at about the time the graft is introduced into the recipient. The short course of help reducing treatment can induce tolerance to unmatched class I and/or minor antigens on a graft which is introduced into the recipient subsequent to expression of the MHC antigen. The duration of the short course of help reducing treatment should be approximately equal to or is less than the period required for mature T cells of the recipient species to initiate rejection of an antigen after first being stimulated by the antigen; in more preferred embodiments, the duration is approximately equal to or is less than two, three, four, five, or ten times the period required for a mature T cell of the recipient species to initiate rejection of an antigen after first being stimulated by the antigen. In other preferred embodiments, the short course of help reducing treatment is administered in the absence of a treatment which stimulates the release of a cytokine by mature T cells in the recipient, e.g., in the absence of a steroid drug in a sufficient concentration to counteract the desired effect of the help reducing treatment, e.g., in the absence of Prednisone (17, 21-dihydroxypregna-1, 4-diene-3, 11, 20-trione) at a concentration which stimulates the release of a cytokine by mature T cells in the recipient. In preferred embodiments, the short course of help reducing treatment is administered in the absence of a steroid drug, e.g., in the absence of Prednisone. In preferred embodiments: the help reducing treatment is begun before or at about the time the graft is introduced; the short course is perioperative; or the short course is postoperative.

Preferred embodiments include those in which: the recipient stem cell is removed from the recipient mammal prior to the DNA insertion and returned to the recipient mammal after the DNA insertion; the DNA is obtained from the individual mammal from which the graft is obtained; the DNA is obtained from an individual mammal which is syngeneic with the individual mammal from which the graft is obtained; the DNA is obtained from an individual mammal which is MHC matched, and preferably identical, with the individual mammal from which the graft is obtained; the DNA includes an MHC class I gene; the DNA includes an MHC class II gene; the DNA is inserted into the cell by transduction, e.g., by a retrovirus, e.g., by a Moloney-based retrovirus; and the DNA is expressed in bone marrow cells and/or peripheral blood cells of the recipient for at least 14, preferably 30, more preferably 60, and most preferably 120 days, after the DNA is introduced into the recipient.

Other preferred embodiments include: the step of, prior to hematopoietic stem cell transplantation, creating hematopoietic space, e.g., by irradiating the recipient mammal with low dose, e.g., between about 100 and 400 rads, whole body irradiation to deplete or partially deplete the bone marrow of the recipient; inactivating thymic T cells by one or more of: prior to hematopoietic stem cell transplantation, irradiating the recipient mammal with, e.g., about 700 rads of thymic irradiation, or administering to the recipient a short course of an immunosuppressant, as is described herein.

Other preferred embodiments include: the step of, prior to implantation of a graft, depleting natural antibodies from the blood of the recipient mammal, e.g., by hemoperfusing an organ, e.g., a liver or a kidney, obtained from a mammal of the second species. (In organ hemoperfusion antibodies in the blood bind to antigens on the cell surfaces of the organ and are thus removed from the blood.)

In other preferred embodiments: the method further includes, prior to hematopoietic stem cell transplantation, introducing into the recipient an antibody capable of binding to mature T cells of said recipient mammal.

Other preferred embodiments further include the step of introducing into the recipient a graft obtained from the donor, e.g., a liver or a kidney.

In preferred embodiments: the donor graft cells are other than a hematopoietic stem cells, or other blood cells; the donor graft cells are swine thymic cells, e.g., swine thymic stromal cells; the donor graft cells are bone marrow stromal cells; the donor graft cells are swine liver cells; the donor graft cells are swine kidney cells; the donor graft cells are swine epithelial cells; the donor graft cells are swine muscle cells, e.g., heart cells; the donor graft cells are swine neuronal cells; the graft cells include an organ, e.g., a kidney, a liver, or a heart; the donor graft cells include dendritic cells or their precursors.

Other preferred embodiments include: the step of introducing into the recipient, donor species-specific stromal tissue, preferably hematopoietic stromal tissue, e.g., fetal liver or thymus. In preferred embodiments: the stromal tissue is introduced simultaneously with, or prior to, the hematopoietic stem cells.

In another aspect, the invention features a method of inducing tolerance in a recipient mammal, e.g., a primate, e.g., a human, to a graft obtained from a donor swine, e.g., a miniature swine. The method includes:

preferably prior to or simultaneous with transplantation of the graft, introducing, e.g., by intravenous injection, into the recipient mammal, swine hematopoietic stem cells, e.g., bone marrow cells or fetal liver or spleen cells (preferably the hematopoietic stem cells home to a site in the recipient mammal);

(optionally) inactivating the natural killer cells of the recipient mammal, e.g., by prior to introducing the hematopoietic stem cells into the recipient mammal, introducing into the recipient mammal an antibody capable of binding to natural killer cells of said recipient mammal; and implanting the graft in the recipient, provided that one or both of: the stem cells, or some or substantially all of the cells of the graft, express a recipient species class I gene which inhibits recipient NK cell mediated attack.

In preferred embodiments either or both, a stem cell or the graft tissue, expresses an HLA C allele. The allele, by way of example, can be any Cw1, Cw2, Cw3, Cw4, Cw5, Cw6, Cw7, Cw8, Cw9, Cw7/8v, or Cw10 allele. In preferred embodiments the allele is a member of a reactivity group, e.g., a Group 1 allele, e.g., any of an HLA C Cw2, Cw4, Cw5, or Cw6 allele, or a Group 2 allele, e.g., any of an HLA C Cw1, Cw3, Cw7, or Cw8 allele. In other preferred embodiments the allele has an Asn at residue 77 and a Lys at residue 80 or a Ser at residue 77 and an Asn at residue 80.

In preferred embodiments either or both, a stem cell or the graft tissue, expresses an HLA A gene. In other preferred embodiments either or both, a stem cell or the graft tissue, graft expresses an HLA B gene. In other preferred embodiments either or both, a stem cell or the graft tissue, expresses an HLA G gene, e.g, any of alleles I–IV of HLA G. In preferred embodiments either or both, a stem cell or the graft tissue, includes one or more, or all, of a transgene which encodes an HLA A gene, a transgene which encodes an HLA B gene, a transgene which encodes an HLA C gene, a transgene which encodes an HLA G gene.

In preferred embodiments: either or both, a stem cell or the graft tissue, includes a first transgene which includes an HLA class I allele, e.g., an HLA C allele, and a second transgene which includes a gene which encodes a class I MHC protein. In preferred embodiments the second transgene includes a human β subunit, e.g., a β-2 microglobulin gene. In other preferred embodiments the first transgene includes an HLA class I allele from a first reactivity group and the second transgene includes an allele from a second reactivity group. For example, the first transgene includes a Group 1 allele, e.g., any of an HLA C Cw2, Cw4, Cw5, or Cw6 allele, and the second transgene includes a Group 2 allele, e.g., any of an HLA C Cw1, Cw3, Cw7, or Cw8 allele. In other preferred embodiments the first transgene includes an allele which has an Asn at residue 77 and a Lys at residue 80 and the second transgene includes an allele which has a Ser at residue 77 and an Asn at residue 80.

In preferred embodiments either or both, a stem cell or the graft tissue, expresses a chimeric class I protein, e.g., chimeric HLA A, B, C, or G gene. For example, the chimeric gene includes a first portion derived from a first allele of the gene encoding the class I protein and a second portion derived from a second allele of the gene encoding the class I protein. In other embodiments, the class I gene is a synthetic sequence selected for the ability to produce a protein which protects a target cell from attack from more than one class of NK cells. In preferred embodiments the transgene includes a gene, e.g., a chimeric or mutated HLA C gene, which confers protection to more than one class of NK cells, e.g., an allele of HLA C having serine at position 77 and lysine at position 80.

In preferred embodiments either or both, a stem cell or the graft tissue, is from a transgenic swine, e.g., a transgenic swine which includes a transgenic human class I gene, e.g., an HLA A, B,C, or G gene.

In preferred embodiment, the method further includes: administering to the recipient a short course of help reducing treatment, e.g., a short course of high dose cyclosporine treatment. The short course of help reducing treatment is generally administered at about the time the graft is introduced into the recipient. The short course of help reducing treatment can induce tolerance to unmatched class I and/or minor antigens on a graft which is introduced into the recipient subsequent to expression of the MHC antigen. The duration of the short course of help reducing treatment should be approximately equal to or is less than the period required for mature T cells of the recipient species to initiate rejection of an antigen after first being stimulated by the antigen; in more preferred embodiments, the duration is approximately equal to or is less than two, three, four, five, or ten times the period required for a mature T cell of the recipient species to initiate rejection of an antigen after first being stimulated by the antigen. In other preferred embodiments, the short course of help reducing treatment is administered in the absence of a treatment which stimulates the release of a cytokine by mature T cells in the recipient, e.g., in the absence of a steroid drug in a sufficient concentration to counteract the desired effect of the help reducing treatment, e.g., in the absence of Prednisone (17, 21-dihydroxypregna-1,4-diene-3, 11, 20-trione) at a concentration which stimulates the release of a cytokine by mature T cells in the recipient. In preferred embodiments, the short course of help reducing treatment is administered in the absence of a steroid drug, e.g., in the absence of Prednisone. In preferred embodiments: the help reducing treatment is begun before or at about the time the graft is introduced; the short course is perioperative; or the short course is postoperative.

The hematopoietic cells prepare the recipient for the graft that follows, by inducing tolerance at both the B-cell and T-cell levels. Preferably, hematopoietic cells are fetal liver or spleen, or bone marrow cells, including immature cells (i.e., undifferentiated hematopoietic stem cells; these desired cells can be separated out of the bone marrow prior to administration), or a complex bone marrow sample including such cells can be used.

One source of anti-NK antibody is anti-human thymocyte polyclonal anti-serum. As is discussed below, preferably, a second anti-mature T cell antibody can be administered as well, which lyses T cells as well as NK cells. Lysing T cells is advantageous for both bone marrow and xenograft survival. Anti-T cell antibodies are present, along with anti-NK antibodies, in anti-thymocyte anti-serum. Repeated doses of anti-NK or anti-T cell antibody may be preferable. Monoclonal preparations can be used in the methods of the invention.

Other preferred embodiments include: the step of introducing into the recipient mammal, donor species-specific stromal tissue, preferably hematopoietic stromal tissue, e.g., fetal liver or thymus. In preferred embodiments: the stromal tissue is introduced simultaneously with, or prior to, the hematopoietic stem cells; the hematopoietic stem cells are introduced simultaneously with, or prior to, the antibody.

Other preferred embodiments include those in which: the same mammal of the second species is the donor of one or both the graft and the hematopoietic cells; and the antibody is an anti-human thymocyte polyclonal anti-serum, obtained, e.g., from a horse or pig.

Other preferred embodiments include: the step of, prior to hematopoietic stem cell transplantation, creating hematopoietic space, e.g., by irradiating the recipient mammal with low dose, e.g., between about 100 and 400 rads, whole body irradiation to deplete or partially deplete the bone marrow of the recipient; inactivating thymic T cells by one or more of: prior to hematopoietic stem cell transplantation, irradiating the recipient mammal with, e.g., about 700 rads of thymic irradiation, or administering to the recipient a short course of an immunosuppressant, as is described herein.

Other preferred embodiments include: the step of, prior to hematopoietic stem cell transplantation, depleting natural antibodies from the blood of the recipient mammal, e.g., by hemoperfusing an organ, e.g., a liver or a kidney, obtained from a mammal of the second species. (In organ hemoperfusion antibodies in the blood bind to antigens on the cell surfaces of the organ and are thus removed from the blood.)

In other preferred embodiments: the method further includes, prior to hematopoietic stem cell transplantation, introducing into the recipient an antibody capable of binding to mature T cells of said recipient mammal.

In other preferred embodiments: the method further includes inactivating T cells of the recipient, e.g., by, prior to introducing the hematopoietic stem cells into the recipient, introducing into the recipient an antibody capable of binding to T cells of the recipient.

In preferred embodiments, the method includes the step of introducing into the recipient a graft obtained from the donor which is obtained from a different organ than the hematopoietic stem cells, e.g., a liver or a kidney.

In preferred embodiments: the donor graft cells are other than a hematopoietic stem cells, or other blood cells; the donor graft cells are swine thymic cells, e.g., swine thymic stromal cells; the donor graft cells are bone marrow stromal cells; the donor graft cells are swine liver cells; the donor graft cells are swine kidney cells; the donor graft cells are swine endothelial cells; the donor graft cells are swine epithelial cells; the donor graft cells are swine muscle cells, e.g., heart cells; the donor graft cells are swine neuronal cells; the graft cells include an organ, e.g., a kidney, a liver, or a heart; the donor graft cells include dendritic cells or their precursors.

Other preferred embodiments include: the step of introducing into the recipient, donor species-specific stromal tissue, preferably hematopoietic stromal tissue, e.g., fetal liver or thymus. In preferred embodiments: the stromal tissue is introduced simultaneously with, or prior to, the hematopoietic stem cells.

Genetically engineered swine cells of the invention can be made by methods known to those skilled in the art, e.g., by retroviral transduction of swine cells. Methods for producing transgenic swine of the invention use standard transgenic technology. These methods include, e.g., the infection of the zygote or organism by viruses including retroviruses; the infection of a tissue with viruses and then reintroducing the tissue into an animal; and the introduction of a recombinant nucleic acid molecule into an embryonic stem cell of a mammal followed by appropriate manipulation of the embryonic stem cell to produce a transgenic animal. In particular, the invention features a transgenic swine, whose germ cells and somatic cells contain a transgene including a DNA sequence encoding a polypeptide and a tissue-specific promoter operably linked to the DNA sequence, wherein the tissue-specific promoter effects expression of the hematopoietic peptide in bone marrow cells of the swine, the transgene being introduced into embryonal cells of the animal, or an ancestor of the animal.

In another aspect, the invention features, a method of inducing tolerance in a recipient mammal, e.g., a primate, e.g., a human, to a graft obtained from a swine, e.g., a miniature swine. The method includes:

prior to or simultaneous with transplantation of the graft, introducing into the recipient mammal, swine thymic tissue, e.g., thymic epithelium, preferably fetal or neonatal thymic tissue; and implanting the graft in the recipient. The thymic tissue prepares the recipient for the graft that follows, by inducing immunological tolerance at the T-cell level. Either or both of, the thymic tissue, or some or all of the cells of the graft, express a recipient species class I gene which inhibits recipient NK cell mediated attack.

In preferred embodiments either or both of, the thymic tissue, or some or all of the cells of the graft, expresses an HLA C allele. The allele, by way of example, can be any Cw1, Cw2, Cw3, Cw4, Cw5, Cw6, Cw7, Cw8, Cw9, Cw7/8v, or Cw10 allele. In preferred embodiments the allele is a member of a reactivity group, e.g., a Group 1 allele, e.g., any of an HLA C Cw2, Cw4, Cw5, or Cw6 allele, or a Group 2 allele, e.g., any of an HLA C Cw1, Cw3, Cw7, or Cw8 allele. In other preferred embodiments the allele has an Asn at residue 77 and a Lys at residue 80 or a Ser at residue 77 and an Asn at residue 80.

In preferred embodiments either or both of, the thymic tissue, or some or all of the cells of the graft, expresses an HLA A gene. In other preferred embodiments either or both of, the thymic tissue, or some or all of the cells of the graft, expresses an HLA B gene. In other preferred embodiments either or both of, the thymic tissue, or some or all of the cells of the graft, expresses an HLA G gene, e.g, any of alleles 14V of HLA G. In preferred embodiments either or both of, the thymic tissue, or some or all of the cells of the graft, includes one or more, or all, of a transgene which encodes an HLA A gene, a transgene which encodes an HLA B gene, a transgene which encodes an HLA C gene, a transgene which encodes an HLA G gene In preferred embodiments: either or both of, the thymic tissue, or some or all of the cells of the graft, includes a first transgene which includes an HLA class I allele, e.g., an HLA C allele, and a second transgene which includes a gene which encodes a class I MHC protein. In preferred embodiments the second transgene includes a human β subunit, e.g., a β-2 microglobulin gene. In other preferred embodiments the first transgene includes an HLA class I allele from a first reactivity group and the second transgene includes an allele from a second reactivity group. For example, the first transgene includes a Group 1 allele, e.g., any of an HLA C Cw2, Cw4, Cw5, or Cw6 allele, and the second transgene includes a Group 2 allele, e.g., any of an HLA C Cw1, Cw3, Cw7, or Cw8 allele. In other preferred embodiments the first transgene includes an allele which has an Asn at residue 77 and a Lys at residue 80 and the second transgene includes an allele which has an a Ser at residue 77 and an Asn at residue 80.

In preferred embodiments either or both of, the thymic tissue, or some or all of the cells of the graft, expresses a chimeric class I protein, e.g., chimeric HLA A, B, C, or G gene. For example, the chimeric gene includes a first portion derived from a first allele of the gene encoding the class I protein and a second portion derived from a second allele of the gene encoding the class I protein. In other embodiments, the class I gene is a synthetic sequence selected for the ability to produce a protein which protects a target cell from attack from more than one class of NK cells. In preferred embodiments the transgene includes a gene, e.g., a chimeric or mutated HLA C gene, which confers protection to more than one class of NK cells, e.g., an allele of HLA C having serine at position 77 and lysine at position 80.

In preferred embodiments either or both of, the thymic tissue, or some or all of the cells of the graft, is from a transgenic swine, e.g., a transgenic swine which includes a transgenic human class I gene, e.g., an HLA A, B, C, or G gene.

Preferred embodiments include other steps to promote acceptance of the graft thymus and the induction of immunological tolerance or to otherwise optimize the procedure. In preferred embodiments: liver or spleen tissue, preferably fetal or neonatal liver or spleen tissue, is implanted with the thymic tissue; donor hemopoietic cells, e.g., cord blood stem cells or fetal or neonatal liver or spleen cells, are administered to the recipient, e.g., a suspension of fetal liver cells administered intraperitoneally or intravenously; the recipient is thymectomized, preferably before or at the time the xenograft thymic tissue is introduced.

In other preferred embodiments the method includes (preferably prior to or at the time of introducing the thymic tissue or stem cells into the recipient) depleting, inactivating or inhibiting recipient NK cells, e.g., by introducing into the recipient an antibody capable of binding to natural killer (NK) cells of the recipient, to prevent NK mediated rejection of the thymic tissue; (preferably prior to or at the time of introducing the thymic tissue into the recipient) depleting, inactivating or inhibiting recipient T cells, e.g., by introducing into the recipient an antibody capable of binding to T cells of the recipient; (preferably prior to or at the time of introducing the thymic tissue or stem cells into the recipient) depleting, inactivating or inhibiting host CD4$^+$ cell function, e.g., by introducing into the recipient an antibody capable of binding to CD4, or CD4$^+$ cells of the recipient. An antimature T cell antibody which lyses T cells as well as NK cells can be administered. Lysing T cells is advantageous for both thymic tissue and xenograft survival. Anti-T cell antibodies are present, along with anti-NK antibodies, in antithymocyte anti-serum. Repeated doses of anti-NK or anti-T cell antibody may be preferable. Monoclonal preparations can be used in the methods of the invention.

Other preferred embodiments include those in which: the recipient does not receive hemopoietic cells from the donor or the donor species: the same mammal of the second species is the donor of both the graft and the thymic tissue; the donor mammal is a swine, e.g., a miniature swine; an anti-human thymocyte polyclonal anti-serum, obtained, e.g., from a horse or pig is administered to the recipient.

Other preferred embodiments include the step of (preferably prior to thymic tissue or hematopoietic stem cell transplantation) creating hematopoietic space, e.g., by one or more of: irradiating the recipient mammal with low dose, e.g., between about 100 and 400 rads, whole body irradiation, the administration of a myelosuppressive drug, the administration of a hematopoietic stem cell inactivating or depleting antibody, to deplete or partially deplete the bone marrow of the recipient.

Other preferred embodiments include (preferably prior to thymic tissue or hematopoietic stem cell transplantation) inactivating thymic T cells by one or more of: irradiating the recipient with, e.g., about 700 rads of thymic irradiation, administering to the recipient one or more doses of an anti T cell antibody, e.g., an anti-CD4 and/or an anti-CD8 monoclonal antibody, or administering to the recipient a short course of an immunosuppressant.

In preferred embodiments the host or recipient is a post-natal individual, e.g., an adult, or a child.

In preferred embodiments the method further includes the step of identifying a host or recipient which is in need of a graft.

Other preferred embodiments include depleting or otherwise inactivating natural antibodies, e.g., by one or more of: the administration of a drug which depletes or inactivates natural antibodies, e.g., deoxyspergualin; the administration of an anti-IgM antibodies; or the absorption of natural antibodies from the recipient's blood, e.g., by contacting the hosts blood with donor antigen, e.g., by hemoperfusion of a donor organ, e.g., a kidney or a liver, from the donor species.

As is discussed herein, killer inhibitory receptors (KIR's) found on NK cells are specific for polymorphic MHC class I molecules. Swine tissue used for grafts should express an HLA class I allele (or alleles) which will maximize protection from the NK cells of the recipient. Thus, in another aspect, the invention includes a method of prolonging acceptance of a swine xenograft tissue by a human which includes:

determining the HLA A, HLA B, HLA C, or HLA G phenotype or genotype of the recipient;

choosing donor tissue, e.g., choosing a donor transgenic animal, which expresses a recipient HLA gene which will confer protection against recipient NK cells and implanting the tissue in the recipient. For example, the donor tissue or animal can express a transgenic form of an allele expressed by the recipient. Alternatively, the donor tissue or animal can express an allele from the same reactivity group as one or more of the alleles expressed in the recipient.

The recipient's HLA A, B, C, or G phenotype or genotype can be determined by standard methods, e.g., by PCR or lymphocyte toxicity.

In another aspect, the invention includes, a panel of transgenic swine including a first transgenic swine and a second transgenic swine. The first transgenic swine has a transgene which includes a first allele of a human HLA A, B, C, or G gene, and the second transgenic swine has a transgene which includes a second allele of the human HLA A, B, C, or G gene. In preferred embodiments the first allele is from a first reactivity group and the second allele is from a second reactivity group. For example, the transgene of the first swine includes a Group 1 allele, e.g., any of an HLA C Cw2, Cw4, Cw5, or Cw6 allele, and the transgene of the second swine includes a Group 2 allele, e.g., any of an HLA C Cw1, Cw3, Cw7, or Cw8 allele. In other preferred embodiments transgene of the first swine includes an allele which has an Asn at residue 77 and a Lys at residue 80 and the transgene of the second swine includes an allele which has an a Ser at residue 77 and an Asn at residue 80. The panel of transgenic swine can be used to supply a donor having an HLA class I allele which will protect a graft from a recipient's NK cells.

NK cells play an important role in the rejection of xenogeneic tissues. Because NK cell killing is inhibited by the presence of class I antigens of the NK cell type on the target cells, NK-mediated attack of porcine tissues by human NK cells is minimized by the invention. This is achieved by introducing a human class I gene into the porcine target.

In contrast to allogeneic cell-mediated killing, xenogeneic human anti-porcine cytotoxicity includes an important contribution from NK cells. Normal autologous and most allogeneic cells are not susceptible to natural killer (NK) cell mediated cytotoxicity due to the expression of major histocompatibility complex (MHC) class I molecules. The preventive signal is delivered to the NK cells through KIR's with different MHC class I specificities. Xenogeneic porcine MHC class I molecules appear not to be recognized by human KIR's and thus render porcine cells susceptible to NK cell-mediated lysis.

Other features and advantages of the invention will be apparent from the following detailed description, and from the claims.

DRAWINGS

The drawings are described briefly below:

FIG. 1A is a graph of the E:T ratio to the % specific lysis, 2A2 ut=solid diamonds, K562=open squares, 2A2/Cw3+= solid triangles, 2A2/A2+=open circles, 2A2/B27+=solid squares; 1B is a graph of the E:T ratio to the % specific lysis, 2A2 ut solid diamonds, K562=open squares, 2A2/Cw3+= solid triangles, 2A2/A2+=open circles, 2A2/B27+=solid squares; 1C is a graph of the E:T ratio to the % specific lysis, 2A2 ut=solid diamonds, 2A2/Cw3+=open squares, 2A2/ A2+=solid triangles.

DETAILED DESCRIPTION

As used herein, the term "transgene" means a nucleic acid sequence (encoding, e.g., one or more class I MHC proteins), which is partly or entirely heterologous, i.e., foreign, to the transgenic animal or cell into which it is introduced. A transgene can include one or more transcriptional regulatory sequences and any other nucleic acid, such as introns, that may be necessary for optimal expression of the selected nucleic acid, all operably linked to the selected nucleic acid, and may include an enhancer sequence.

As used herein, the term "transgenic cell" refers to a cell containing a transgene.

As used herein, a "transgenic animal" is any animal in which one or more, and preferably essentially all, of the cells of the animal includes a transgene. The transgene is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. Transgenic swine which include one or more transgenes encoding one or more class I MHC peptides are within the scope of this invention. For example, a double or triple transgenic animal, which includes two or three transgenes can be produced.

As used herein, the term "germ cell line transgenic animal" refers to a transgenic animal in which the transgene genetic information exists in the germ line, thereby conferring the ability to transfer the information to offspring. If such offspring in fact possess some or all of that information then they, too, are transgenic animals.

As used herein, the term "operably linked" means that selected DNA, e.g., encoding a class I peptide, is in proximity with a transcriptional regulatory sequence, e.g., tissue-specific promoter, to allow the regulatory sequence to regulate expression of the selected DNA.

The term "genetically programmed" as used herein means to permanently alter the DNA, RNA, or protein content of a cell.

As used herein, the term "recombinant swine cells" refers to cells derived from swine, preferably miniature swine, which have been used as recipients for a recombinant vector or other transfer nucleic acid, and include the progeny of the original cell which has been transfected or transformed. Recombinant swine cells include cells in which transgenes or other nucleic acid vectors have been incorporated into the host cell's genome, as well as cells harboring expression vectors which remain autonomous from the host cell's genome.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, e.g. the transformed swine cell expresses human cell surface peptides.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors".

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of the recombinant gene is under the control of a promoter sequence (or other transcriptional regulatory sequence) which naturally controls the expression of the recombinant gene in humans, or which naturally controls expression of the corresponding gene in swine cells. In even more preferred embodiments, the transcription regulatory sequence causes hematopoietic-specific expression of the recombinant protein. The above embodiments not withstanding, it will also be understood that the recombinant gene can be under the control of transcriptional regulatory sequences different from those sequences naturally controlling transcription of the recombinant protein. Transcription of the recombinant gene, for example, can be under the control of a synthetic promoter sequence. Preferably, the promoter sequence controlling transcription of the recombinant gene is active (i.e., can promote gene expression) in bone marrow cells, especially hematopoietic cells or in epithelial cells. The promoter that controls transcription of the recombinant gene may be of viral origin; examples are promoters sometimes derived from bovine herpes virus (BHV), Moloney murine leukemia virus (MLV), SV40, Swine vesicular disease virus (SVDV), and cytomegalovirus (CMV).

As used herein, the term "tissue-specific promoter" means a DNA sequence that serves as a promoter, i.e., regulates expression of a selected DNA sequence operably linked to the promoter, and which effects expression of the selected DNA sequence in specific cells, e.g., hematopoietic cells or in epithelial cells. The tissue specific promoter directs expression predominantly, if not exclusively in hematopoietic cells or in epithelial cells. Particularly useful promoter sequences for directing expression include: promoter sequences naturally associated with the recombinant human gene; promoter sequences naturally associated with the homologous pig gene (i.e. corresponding to the recombinant human gene); promoters which are active primarily in hematopoietic cells, e.g. in lymphoid cells, in erythroid cells, or in myeloid cells or in epithelial cells; the immunoglobulin promoter described by Brinster et al. (1983) *Nature* 306:332–336 and Storb et al. (1984) *Nature* 310:238–231; the immunoglobulin promoter described by Ruscon et al. (1985) *Nature* 314:330–334 and Grosscheld et al. (1984) *Cell* 38:647–658; the globin promoter described by Townes et al. (1985) *Mol. Cell. Biol.* 5:1977–1983, and Magram et al. (1989) *Mol. Cell. Biol* 9:4581–4584. Other promoters are described herein or will be apparent to those skilled in the art. Moreover, such promoters also may include additional DNA sequences that are necessary for expression, such as introns and enhancer sequences. The term also covers so-called "leaky" promoters, which regulate expression of a selected DNA primarily in one tissue, but cause expression in other tissues as well. Other regulatory elements e.g., locus control regions, e.g., DNase I hypersensitive sites, can be included.

By "cell specific expression", it is intended that the transcriptional regulatory elements direct expression of the recombinant protein in particular cell types, e.g., bone marrow cells or epithelial cells.

"Graft", as used herein, refers to a body part, organ, tissue, or cells. Grafts may consist of organs such as liver, kidney, heart or lung; body parts such as bone or skeletal matrix; tissue such as skin, intestines, endocrine glands; or progenitor stem cells of various types.

The term "tissue" as used herein, means any biological material that is capable of being transplanted and includes organs (especially the internal vital organs such as the heart, lung, liver, kidney, pancreas and thyroid), cornea, skin, blood vessels and other connective tissue, cells including blood and hematopoietic cells, Islets of Langerhans, brain cells and cells from endocrine and other organs and bodily fluids, all of which may be candidate for transplantation.

"A discordant species combination", as used herein, refers to two species in which hyperacute rejection occurs when a graft is grafted from one to the other. In the subject invention, the donor is of porcine origin and the recipient is human.

"Hematopoietic stem cell", as used herein, refers to a cell, e.g., a bone marrow cell, a fetal or neonatal liver or spleen cell, or a cord blood cell which is capable of developing into a mature myeloid and/or lymphoid cell.

"Progenitor cell", as used herein, refers to a cell which gives rise to an differentiated progeny. In contrast to a stem cell, a progenitor cell is not always self renewing and is relatively restricted in developmental potential.

"Stromal tissue", as used herein, refers to the supporting tissue or matrix of an organ, as distinguished from its functional elements or parenchyma.

"Tolerance", as used herein, refers to the inhibition of a graft recipient's immune response which would otherwise occur, e.g., in response to the introduction of a nonself MHC antigen into the recipient. Tolerance can involve humoral, cellular, or both humoral and cellular responses. Tolerance, as used herein, refers not only to complete immunologic tolerance to an antigen, but to partial immunologic tolerance, i.e., a degree of tolerance to an antigen which is greater than what would be seen if a method of the invention were not employed.

"Miniature swine", as used herein, refers to wholly or partially inbred animal. "Short course of a immunosuppressive agent", as used herein, means a transitory non-chronic course of treatment. The treatment should begin before or at about the time the treatment to induce tolerance is begun, e.g., at about the time stem cells are introduced into the recipient. e.g., the short course can begin on the day the treatment to induce tolerance is begun, e.g., on the day, stem cells are introduced into the recipient or the short course can begin within 1, 2, 4, 6, 8, or 10 days before or after the treatment to induce tolerance is begun, e.g., within 1, 2, 4, 6, 8, or 10 days before or after stem cells are introduced into the recipient. The short course can last for: a period equal to or less than about 8–12 days, preferably about 10 days, or a time which is approximately equal to or is less than two, three, four, five, or ten times the 8–12 or 10 day period. Optimally, the short course lasts about 30 days. The dosage should be sufficient to maintain a blood level sufficient to inactivate thymic or lymph node T cells. A dosage of approximately 15 mg/kg/day has been found to be effective in primates.

"Lymph node or thymic T cell", as used herein, refers to T cells which are resistant to inactivation by traditional methods of T cell inactivation, e.g., inactivation by a single intravenous administration of anti-T cell antibodies, e.g., antibodies, e.g., ATG preparation.

"Help reduction", as used herein, means the reduction of T cell help by the inhibition of the release of at least one cytokine, e.g. , any of IL-2, IL4, IL-6, gamma interferon, or TNF, from T cells of the recipient at the time of the first exposure to an antigen to which tolerance is desired. The inhibition induced in a recipient's T cell secretion of a cytokine must be sufficient such that the recipient is tolerized to an antigen which is administered during the reduction of help. Although not being bound by theory, it is believed that the level of reduction is one which substantially eliminates the initial burst of IL-2 which accompanies the first recognition of a foreign antigen but which does not eliminate all mature T cells, which cells may be important in educating and producing tolerance.

"A help reducing agent", as used herein, is an agent, e.g., an immunosuppressive drug, which results in the reduction of cytokine release. Examples of help reducing agents are cyclosporine, FK-506, and rapamycin. Anti-T cell antibodies, because they can eliminate T cells, are not preferred for use as help reducing agents. A help reducing agent must be administered in sufficient dose to give the level of inhibition of cytokine release which will result in tolerance. The help reducing agent should be administered in the absence of treatments which promote cytokine, e.g., IL-2, release. Putative agents help reducing agents can be prescreened by in vitro or in vivo tests, e.g., by contacting the putative agent with T cells and determining the ability of the treated T cells to release a cytokine, e.g., IL-2. The inhibition of cytokine release is indicative of the putative agent's efficacy as a help reducing agent. Such prescreened putative agents can then be further tested in a kidney transplant assay. In a kidney transplant assay a putative help reducing agent is tested for efficacy by administering the putative agent to a recipient monkey and then implanting a kidney from a class II matched class I and minor antigen mismatched donor monkey into the recipient. Tolerance to the donor kidney (as indicated by prolonged acceptance of the graft) is indicative that the putative agent is, at the dosage tested, a help reducing agent.

"Short course of a help reducing agent", as used herein, means a transitory non-chronic course of treatment. The treatment should begin before or at about the time of transplantation of the graft. Alternatively, the treatment can begin before or at about the time of the recipient's first exposure to donor antigens. Optimally, the treatment lasts for a time which is approximately equal to or less than the period required for mature T cells of the recipient species to initiate rejection of an antigen after first being stimulated by the antigen. The duration of the treatment can be extended to a time approximately equal to or less than two, three, four, five, or ten times, the period required for a mature T cell of the recipient species to initiate rejection of an antigen after first being stimulated by the antigen. The duration will usually be at least equal to the time required for mature T cells of the recipient species to initiate rejection of an antigen after first being stimulated by the antigen. In pigs and monkeys, about 12 days of treatment is sufficient. Experiments with cyclosporine A (10 mg/kg) in pigs show that 6 days is not sufficient. Other experiments in monkeys show that IL-2 administered on day 8, 9, or 10 of cyclosporine A treatment will result in rejection of the transplanted tissue. Thus, 8, 9, or 10 days is probably not sufficient in pigs. In monkeys, a dose of 10 mg/kg cyclosporine with a blood level of about 500–1,000 ng/ml is sufficient to induce tolerance to class II matched class I and minor antigen mismatched kidneys. The same blood level, 500–1,000 ng/ml, is sufficient to induce tolerance in pigs. Long-term administration of 5mg/kg prevents rejection (by long term immune suppression) but does not result in tolerance.

As described herein, the transgenic donor tissue may come from a cell culture or from a transgenic swine. The transgenic swine should express (or be capable of expressing) the recombinant human gene in at least the tissue to be transplanted.

The practice of the present invention will employ, unless otherwise indicated, techniques which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

Although methods and materials similar or equivalent to those described herein can be used in the practice or testing of the present invention, the preferred methods and materials are described below. All publications mentioned herein are incorporated by reference. In addition, the materials, methods, and examples are illustrative only and not intended to be limiting.

Killer Inhibitory Receptors

Natural killer (NK) cell-mediated immunity, comprising cytotoxicity and cytokine secretion, plays a major role in biological resistance to a number of autologous and allogeneic cells. The common mechanism of target cell recognition appears to be the lack or modification of self MHC class I-peptide complexes on the cell surface, which can lead to the elimination of virally infected cells, tumor cells and major histocompatibility MHC-incompatible grafted cells. KIR's, members of the Ig superfamily which are expressed on NK cells, have recently been discovered and cloned. KIR's are specific for polymorphic MHC class I molecules and generate a negative signal upon ligand binding which leads to target cell protection from NK cell-mediated cytotoxicity in most systems. In order to prevent NK cell autoimmunity, i.e., the lysis of normal autologous cells, it is believed that every given NK cell of an individual expresses at least on KIR recognizing at least one of the autologous HLA-A, B, C, or G alleles.

NK cell-mediated cytotoxicity appears to plays an important role in the cellular immune response against xenografts, whereas NK cells do not seem to be of major relevance in the rejection of vascularized allografts. Xenogeneic human anti-porcine cytotoxicity in vitro includes an important contribution from activated NK cells. There are at least two possible explanations for the susceptibility of porcine cells to xenogeneic human NK cell-mediated cytotoxicity. First, porcine MHC class I molecules, in contrast to human MHC class I molecules, may not trigger the KIR's expressed by human NK cells due to differences in the amino acid sequence which are critical for the engagement of such receptors. Alternatively, porcine cells may express surface molecules including oligosaccharides which activate NK cell-mediated lysis through NKR-P1 or other related activating NK cell receptors.

A Transgenic Human Class I Gene Protects Swine Cells from Human NK-Mediated Lysis An immortalized porcine bone-marrow derived endothelial cell line (2A2) was transfected with three different human MHC class I constructs. The three constructs included, respectively, HLA-A2.1, HLA-B27 and HLA-Cw3 genomic DNA. Surface expression of human MHC class I molecules on 2A2 transfectants was demonstrated by staining with W6/32, a monomorphic anti-human MHC class I antibody. To analyze the susceptibility of the 2A2 transfectants against human NK cells, NK clones were generated and tested for their xenogeneic killing specificities: HLA-Cw3 positive porcine 2A2 cells, but not 2A2 untransfected, 2A2 HLA-B27 or 2A2 HLA-A2.1 positive cells, were protected from lysis mediated by group 2 (GL 183+, EB6−) NK clones expressing the HLA-Cw3 specific KIR p.58. In contrast, 2A2 HLA-Cw3 positive cells were readily lysed by group 1 (GL 183−, EB6+) NK clones. These data are discussed in more detail below.

Figure 1B:
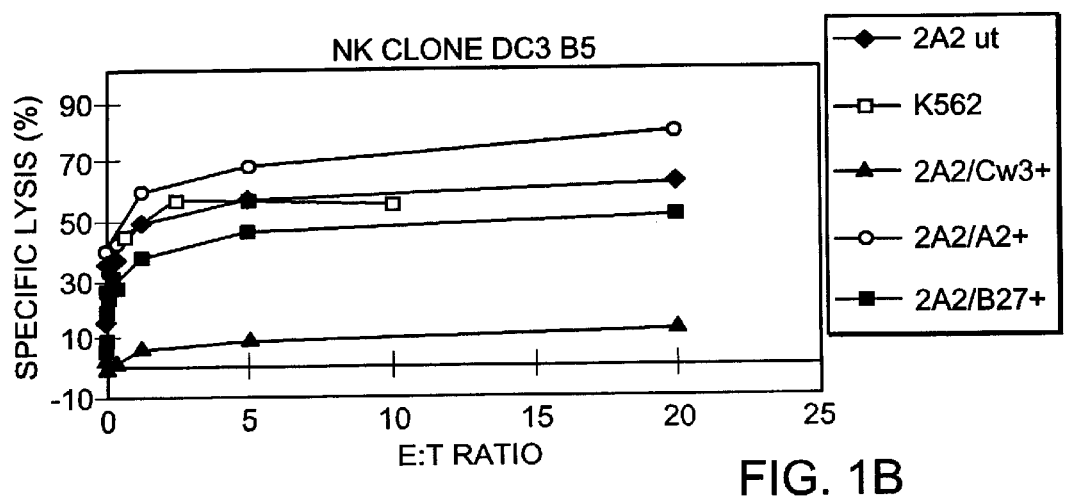
Figure 1C:
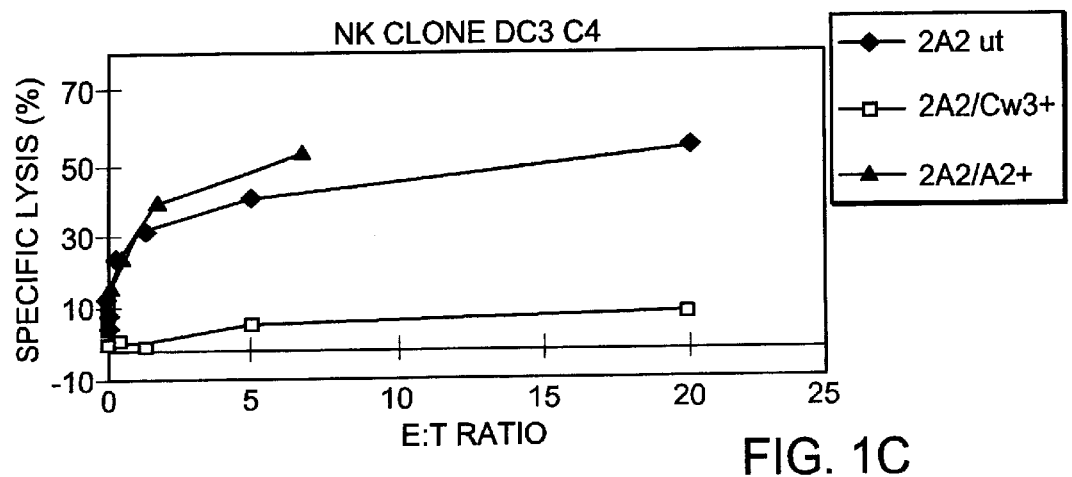

HLA-Cw3 Expression on Porcine Endothelial Cell (EC) line 2A2 Provides Specific Protection Against Human NK Cell Mediated Lysis:

Human NK clones were tested as effector cells in a standard $^{51}$Cr-release cytotoxicity assay. Target cells (5,000) were added in triplicates to serial 2-fold dilutions of effector NK cells in round-bottom 96 well plates, starting with an effector-to target (E:T) ratio of 20:1. The percentage of specific cytotoxicity was measured and shown on the y-axis, see FIG. 1. The cytotoxic activity of human NK clones against HLA class I gene transfected 2A2 cells expressing HLA-A2 (2A2/A2+), HLA-B27 (2A2/B27+), or HLA-Cw3 (2A2/Cw3+) molecules were compared to the untransfected 2A2 (2a2/ut, solid diamonds) porcine endothelial cell line as well as the NK susceptible K562 erythroleukemic cell line, FIGS. 1A, 1B. The expression of HLA-Cw3 on porcine target cells (2A2/Cw3) provided specific protection against group 2 NK clones, as shown for DC3B5 and DC3C4, which were otherwise able to effectively lyse the 2A2/A2, 2A2/B27 transfected as well as the 2A2/ut cell lines, FIGS. 1B, 1C. The specific lysis was reduced to less than 10% even after 20:1 effector to target ratio. In contrast, group 1 NK clones, represented here by DC1B2, were unaffected by the expression of HLA Cw3, demonstrating that 2A2/Cw3 cells were in fact still susceptible to lysis, FIG. 1A. These results clearly demonstrate the inhibitory activity of Cw3 expression on the porcine derived endothelial target cells against specific human NK cells.

Cells:

The bone marrow-derived endothelial cell (EC) line 2A2, immortalized by SV40 transformation, was obtained by standard methods. EC character was established to be greater than 95% as assessed by morphology and by FACS analysis using an endothelial cell specific marker (dil-LDL, Biomedical Technologies, Inc., Stoughton, Mass.). The NK sensitive K562 human erythroleukemic cell line was originally obtained from ATCC.

HLA Gene Transfection:

Full length genomic DNA of HLA-A2.1, Koller et al., 1985, J. Immunol. 134:2727–2733, hereby incorporated by reference, was inserted into the pUC9 vector, full length genomic DNA of HLA-B27, Weiss et al., 1985, Immunobiology 170:367–380, hereby incorporated by reference, was inserted into the pUC13 vector, and full length genomic DNA of HLA-Cw3, Sodoyer et al., 1984, EMBO J.3: 879–885, hereby incorporated by reference, was inserted into the pBR328 vector. Either of the HLA class I constructs was co-transfected with a neomycin resistance gene encoded within the pWLNeo (Stratagene, La Jolla, Calif.) vector at a ratio of 1:20 into 2A2 porcine EC using a standard calcium-phosphate transfection protocol. 14 hours after transfection, cells were treated with ice-cold dimethyl sufoxide (Fisher Scientific, Fair Lawn, N.J.) for 5 minutes, followed by 2 washes. As soon as the cells started to grow again (72–96 hours) they were selected for at least 2 weeks in medium containing 0.2 mg/ml of active G418 (Gibco-BRL) before testing for the expression of human HLA class I by cell surface staining and flow cytometry.

Human CD3-Cd56/16+NK Cell Cloning:

Peripheral blood mononuclear cells (PBMC) were obtained from healthy donors by Ficoll-Hypaque density gradient centrifugation. All blood donors were typed for HLA-A, B, C using a standard National Institute of Health lymphocytotoxicity technique. Purified human NK-cells were isolated by negative magnetic bead selection using the MACS system (Miltenyi Biotec, Auburn, Calif.) as previously described. NK clones were generated by limiting dilution cloning according to an established protocol with minor alterations. Briefly, purified NK cells were diluted at concentrations of 1 cell/well, 3 cells/well and 10/cells/well, respectively, in 96 well U-bottom plates (Costar, Cambridge, Mass.) and incubated at 37° C., 6% $CO_2$ in the presence of irradiated (2500rad) autologous or allogeneic feeder PBMC ($10^5$/well). Culture medium (CM) was AIM-V (Gibco-BRL, Grand Island, N.Y.) containing 100U/ml recombinant human (rh)IL-2 (Chiron, Palo Alto, Calif.), 100 U/ml Penicillin/100 µg/ml Streptomycin (Gibco-BRL), 100 µg L-glutamine (Gibco-BRL), 10 mmol/1 HEPES (Mediatech, Herndon, Va.), 1 mM sodium pyruvate (Bio Whittaker, Walkersville, Md.), non-essential amino acids (Bio Whittaker), 5% autologous or allogeneic heat-inactivated human plasma, and 5% leukocyte conditioned medium (Ritz). After 6 days fresh feeder PBMC were added ($10^5$/well) and as soon as growth was observed, 25ul of CM was replaced every other day with fresh CM containing 1000 U/ml rhIL-2.

Flow Cytometry Analysis and Antibodies:

Surface expression of human and porcine MHC class I molecules on untransfected (ut) porcine 2A2 EC and 2A2 HLA-transfectants was analyzed by indirect immunofluorescence on a Becton Dickinson FACScan (Sunnyvale, Calif.) using the monomorphic anti-human MHC class I mAb W6/32, and the monomorphic anti-pig MHC class I mAb 2.27.3A. Propidium iodide gating was performed to exclude dead cells. Cells expressing the HLA class I molecules (W6/32+) were isolated by immunosorting on a FACS Star Plus (Becton Dickinson). HLA class I expression was stable as assessed by repeated flow cytometry analysis.

Phenotypic analysis of human NK clones was carried out by indirect immunophenotypic staining and flow cytometry using hybridoma supernatants of EB6 and GL183 and secondary FITC-goat-anti-mouse purchased from Boehringer Mannheim (Indianapolis, Ind.). The following mAbs directly conjugated with either fluorescein isothiocyanate (FITC) or phycoerythrin (PE) were used for two-color analysis: PE-anti-CD16 (Leu-11c) and PE-anti-CD56 (Leu-19), purchased from Becton Dickinson, isotype-matched control antibodies and FITC-anti-CD3 (UCHT1), purchased from PharMingen (San Diego, Calif.).

Cytotoxicity Assays:

Human NK clones were tested as effector cells in standard $^{51}$Cr-release cytotoxicity assays as described previously. K562 cells were used as controls for NK cell-mediated cytotoxicity. After trypsinization (0.05% trypsin, 0.5 mmol/1 EDTA, Life Technologies) 2A2 HLA-transfectants were washed and labeled with 200 µi Na$_2$$^{51}$CrO$_4$ (Du Pont, Boston, Mass.)/10×10$^6$ cells in 0.5 ml AIM-V medium for 90 minutes at 37° C. Untransfected (ut) 2A2 EC as well as sorted 2A2 EC lacking HLA expression after transfection were used as controls. After three washes, 5×10$^3$ target cells were added to triplicate samples of serial 2-fold dilutions of effector cells in round-bottom 96 well plates, starting with an effector-to-target (E:T) ratio of 20:1.

KIR Specificity

KIR's are specific for polymorphic MHC class I molecules. For best results the swine tissue should express an HLA A, B, C, or G allele (or alleles) which will maximize protection from the NK cells of the recipient. As is described below, this can be accomplished in several ways.

The recipient's HLA C genotype can be determined by standard methods, e.g., by PCR or lymphocyte toxicity., and a donor animal which expresses one or more of the alleles present in the recipient used to supply the transplanted tissue.

"Universal or semi-universal donor" animals which express one or more alleles which confer protection from more than one class of NK cell can be used. NK cell reactivity falls into two broad groups, Group 1 and Group II. HLA C Cw2, Cw4, Cw5, and Cw6 alleles are in Group 1. HLA C Cw1, Cw3, Cw7, and Cw8 alleles in Group 2. A group 1 allele will provide protection against NK cells with any Group 1 specificity. A Group 2 allele will provide protection against NK cells with any Group 2 specificity. Tissue which expresses a Group 1 allele should provide protection against NK cells expressing any Group 1 allele. Tissue which expresses a Group 2 allele should provide protection against NK cells expressing any Group 2 allele. Swine tissue which expresses a Group 1 and a Group 2 allele should provide broad protection.

Universal or semi-universal donor animals which express a chimeric, synthetic, mutated or otherwise modified gene which confers protection from more than one class of NK cells can also be used. For example, a transgene, e.g., a chimeric or mutated HLA C gene, which confers protection to more than one class of NK cells, e.g., an allele of HLA C having serine at position 77 and lysine at position 80, can be used to confer protection against both Group 1 and Group 2 NK cells. See e.g., Biassoni, 1995, J. Exp. Med. Vol. 182: 605–609, hereby incorporated by reference. See also Moretta et al., 1996, Ann. Rev. Immunol. 14: 619–648, hereby incorporated by reference, which together with the disclosure herein, provides guidance for altering critical residues in the HLA C genes.

Although HLA C seems most important in NK mediated interactions, HLA A and HLA B may also play a role in NK mediated lysis. Matching is of less importance with these genes. The B alleles are all in one NK reactivity group. The A alleles are in one or at the most two groups. If necessary, approaches analogous to those described for the C gene can be used with the A, B, and G genes.

Recombinant Human Genes

Introduction of a nucleic acid encoding a human class I protein into a swine cell of the present invention requires that the recombinant human gene be introduced into the cell, or a precursor of the cell. As will be understood, the mode of introduction and the desired integration phenotype of the resulting swine cell (i.e. whether the vector is integrated into the cell's genome or remains episomal) can influence the choice of expression vector used to generate the subject recombinant swine cells. In general, expression vectors containing the human class I encoding nucleic acid can be constructed by operably linking an appropriate transcriptional regulatory sequence, e.g. a tissue-specific promoter, with a nucleic acid, e.g. cDNA or genomic DNA, encoding the human class I protein. Moreover, a tissue-specific promoter can be linked to more than one cDNA, each encoding a different human class I protein. Depending on the specific promoter used, it may be desirable to modify the promoter-cDNA construct to include an intron splice site and/or a polyadenylation signal.

In addition to the 5' and 3' expression regulation sequences and the recombinant DNA (either genomic or derived from cDNA) the transgenes of the invention can also include a "recombinant intervening sequence" which interrupts the transcribed but untranslated 5' region of the transgene. Such intervening sequences (IVS) are known in the art. Such sequences as used herein are "homologous recombinant intervening sequences" in that the 5' and 3' RNA splice signals in the IVS are those normally found in an IVS from an endogenous or heterologous gene. Recombinant intervening sequences may, however, also comprise a "hybrid intervening sequences". Such hybrid intervening sequences comprise a 5' RNA splice signal and 3' RNA splice signal from intervening sequences from different sources. In some aspects of the invention, such hybrid IVS comprise at least one "permissive RNA splice sequence". As used herein, a permissive RNA splice signal is an RNA splice signal sequence, preferably a 3' RNA splice signal, from an intron contained within a repertoire of germ line DNA segments which undergo rearrangement during cell differentiation. Examples of such gene repertoires include the immunoglobulin supergene family, including the immunoglobulins and T-cell antigen receptors as well as the repertoire of the major histocompatibility complex (MHC) genes and others. Particularly preferred permissive splice sequences are those obtained from the immunoglobulin repertoire, preferably of the IgG class, and more preferably those 3' splice signal sequences associated with the J-C segment rearrangement of the Ig heavy and light chain, most preferably the heavy chain. Hybrid intervening sequences containing permissive RNA splice signals are preferably used when the recombinant DNA corresponds to a cDNA sequence.

Based on the foregoing, it is apparent that preferred transgenes can include relatively large amounts of 5' and 3' expression regulation sequences. Further, the recombinant DNA is preferably derived from genomic clones which may be tens to hundreds of kilobases in length. Based on the present technology for cloning and manipulating DNA, the construction and microinjection of transgenes is practically limited to linearized DNA having a length not greater than about 100 kb. However, the transgenes of the invention, especially those having a length greater than about 50 kb, may be readily generated by introducing two or more overlapping fragments of the desired transgene into an embryonal target cell. When introduced, the overlapping fragments undergo homologous recombination which results in integration of the fully reconstituted transgene in the genome of the target cell. In general, it is preferred that such overlapping transgene fragments have 100% homology in those regions which overlap. However, lower sequence homology may be tolerated provided efficient homologous recombination occurs. If non-homology does exist between the homologous sequence portions, it is preferred that the non-homology not be spread throughout the homologous sequence portion but rather be located in discrete areas. Although as few as 14 base pairs at 100% homology are sufficient for homologous recombination in mammalian cells (Rubnitz et al. (1984) *Mol. Cell. Biol.* 4:2253–2258), longer homologous sequence portions are preferred, e.g. 500 bp, more preferably 1000 bp, next most preferably 2,000 bp and most preferably greater than 2,000 bp for each homologous sequence portion. It may also be desirable to use YAC's and MAC's for manipulation of recombinant nucleic acids of the invention.

In further embodiments, the recombinant class I protein can be a chimeric peptide having a portion encoded by a first human class I gene and a second human class I gene. This allows for the use of hybrid class I molecules which are optimized for binding to more than one NK receptor.

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. Alternatively, PCR amplification of gene fragments can be carried out using anchor primers which give rise to complementary overhangs between two consecutive gene fragments (e.g. between the human gene and the swine gene) which can subsequently be annealed to generate a chimeric gene sequence (see, for example, Current Protocols in Molecular Biology, Eds. Ausubel et al. John Wiley & Sons: 1992).

A transgenic swine which expresses a first transgene can be crossed with a transgenic swine which expresses a second transgene to provide a transgenic animal which expresses both. (Modifications of this technique can be used to add third and subsequent genes as well.) Thus, a transgenic swine which expresses only one transgene or the other of the alpha or beta chains, can be cross-bred with the appropriate transgenic mate to yield offspring which are chimeric for both chains. Alternatively, only the alpha chain need be expressed as it may form active receptor complexes with the swine $\beta$-2 chain.

The recombinant nucleic acid constructs encoding human class I genes may be inserted into any suitable plasmid, bacteriophage, or viral vector for amplification, and may thereby be propagated using methods known in the art, such as those described in *Molecular Cloning A Laboratory Manual*, 2nd Ed., ed. by Sambrook, Fritsch and Maniatis (Cold Spring Harbor Laboratory Press: 1989). In the preferred embodiments, expression vectors compatible with eukaryotic cells, preferably those compatible with vertebrate cells are used. Eukaryotic cell expression vectors are well known in the art and are available from several commercial sources. The preferred swine expression vectors contain both prokaryotic sequences (to facilitate the propagation of the vector in bacteria), and one or more eukaryotic transcription units that are functional in swine cells. Typically, such vectors provide convenient restriction sites for insertion of the desired recombinant DNA molecule. The pcDNAI, pSV2, pSVK, pMSG, pSVL, pPVV-1/PML2d and pTDT1 (ATCC No. 31255) derived vectors are examples of mammalian expression vectors suitable for transfection of swine cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for expression of proteins in swine cells. The various methods employed in the preparation of the plasmids and transformation of host cells are well known in the art. For other suitable expression systems for useful in the present invention, as well as general recombinant procedures, see *Molecular Cloning A Laboratory Manual*, 2nd Ed., ed. by Sambrook, Fritsch and Maniatis (Cold Spring Harbor Laboratory Press:1989).

Under those circumstances wherein the recombinant nucleic acid molecule is introduced into swine oocytes as a transgene to be incorporated into the host genome, the construct can be linearized and excess vector sequences will preferably be removed, for example, by cutting the recombinant nucleic acid molecule with one or more restriction endonucleases to produce a linear nucleic acid molecule containing as a minimum, the desired transcriptional regulatory sequences and a human hematopoietic gene. Preferably the nucleic acid molecule (e.g. the transgene) is from about 5,000 base pairs to about 100,000 base pairs in length.

Some transgenic pigs may carry multiples of the transgene, with the transgene copies incorporated at different sites in the genome. The site of transgene incorporation into the genome can strongly influence transgene expression; therefore, one may correlate transgene expression with discrete transgene restriction fragment length polymorphism patterns. In addition, as discussed above, two transgenic swine, each expressing a different class I protein, can be mated to produce an animal that expresses both transgene products. The same effect can be achieved by introducing two separate transgenes into the same embryonal cell.

Genetically Engineered Swine Cells

Transgenic swine cells of the invention can be produced by any methods known to those in the art. Transgenes can be introduced into cells, e.g., stem cells, e.g., cultured stem cells, by any methods which allows expression of these genes at a level and for a period sufficient to promote engraftment or maintenance of the cells. These methods include e.g., transfection, electroporation, particle gun bombardment, and transduction by viral vectors, e.g., by retroviruses. Transgenic swine cells can also be derived from transgenic animals.

Retroviral Introduction of Transgenes

Recombinant retroviruses are a preferred delivery system. They have been developed extensively over the past few years as vehicles for gene transfer, see e.g., Eglitis et al., 1988, *Adv. Exp. Med Biol.* 241:19. The most straightforward retroviral vector construct is one in which the structural genes of the virus are replaced by a single gene which is then transcribed under the control of regulatory elements contained in the viral long terminal repeat (LTR). A variety of single-gene-vector backbones have been used, including the Moloney murine leukemia virus (MoMuLV). Retroviral vectors which permit multiple insertions of different genes such as a gene for a selectable marker and a second gene of interest, under the control of an internal promoter can be derived from this type of backbone, see e.g., Gilboa, 1988, *Adv. Exp. Med Biol.* 241:29.

The elements of the construction of vectors for the expression of a protein product are known to those skilled in the art. The most efficient expression from retroviral vectors is observed when "strong" promoters are used to control transcription, such as the SV 40 promoter or LTR promoters, reviewed in Chang et al., 1989, *Int. J. Cell Cloning* 7:264. These promoters are constitutive and do not generally permit tissue-specific expression. Other suitable promoters are discussed above.

The use of efficient packaging cell lines can increase both the efficiency and the spectrum of infectivity of the produced recombinant virions, see Miller, 1990, *Human Gene Therapy* 1:5. Murine retroviral vectors have been useful for transferring genes efficiently into murine embryonic, see e.g., Wagner et al., 1985, *EMBO J.* 4:663; Griedley et al., 1987 *Trends Genet.* 3:162, and hematopoietic stem cells, see e.g., Lemischka et al., 1986, *Cell* 45:917–927; Dick et al., 1986, *Trends in Genetics* 2:165–170.

A recent improvement in retroviral technology which permits attainment of much higher viral titers than were previously possible involves amplification by consecutive transfer between ecotropic and amphotropic packaging cell lines, the so-called "ping-pong" method, see e.g., Kozak et al., 1990, *J. Virol.* 64:3500–3508; Bodine et al., 1989, *Prog. Clin. Biol. Res.* 319: 589–600.

Transduction efficiencies can be enhanced by pre-selection of infected marrow prior to introduction into recipients, enriching for those bone marrow cells expressing high levels of the selectable gene, see e.g., Dick et al., 1985, *Cell* 42:71–79; Keller et al., 1985, *Nature* 318:149–154. In addition, recent techniques for increasing viral titers permit the use of virus-containing supernatants rather than direct incubation with virus-producing cell lines to attain efficient transduction, see e.g., Bodine et al., 1989, *Prog. Clin. Biol. Res.* 319:589–600. Because replication of cellular DNA is required for integration of retroviral vectors into the host genome, it may be desirable to increase the frequency at which target stem cells which are actively cycling e.g., by inducing target cells to divide by treatment in vitro with growth factors, see e.g., Lemischka et al., 1986, *Cell* 45:917–927, a combination of IL-3 and IL-6 apparently being the most efficacious, see e.g., Bodine et al., 1989, *Proc. Natl. Acad. Sci.* 86:8897–8901, or to expose the recipient to 5-fluorouracil, see e.g., Mori et al., 1984, *Jpn. J. Clin. Oncol.* 14 Suppl. 1:457–463, prior to marrow harvest, see e.g., Lemischka et al., 1986, *Cell* 45:917–927; Chang et al., 1989, *Int. J. Cell Cloning* 7:264–280.

The inclusion of cytokines or other growth factors in the retroviral transformations can lead to more efficient transformation of target cells.

Preparation of Transgenic Swine

According to another aspect of the invention, there is provided graftable swine cells, e.g., hematopoietic stem cells, e.g., swine bone marrow cells, or other tissue which express one or more recombinant human HLA class I protein which minimize NK cell-mediated rejection in human subjects.

In particular, the present invention includes recombinant swine cells expressing a human class I gene. In a preferred embodiment, the human class I gene is a part of a recombinant nucleic acid molecule that contains a tissue specific promoter, e.g. hematopoietic specific promoter, located proximate to the human gene and regulating expression of the human gene in the swine cell. Tissues containing the recombinant human class I gene may be prepared by introducing a recombinant nucleic acid molecule into a tissue, such as bone marrow cells, using known transformation techniques. These transformation techniques include transfection and infection by retroviruses carrying either a marker gene or a drug resistance gene. See for example, *Current Protocols in Molecular Biology*, Ausubel et al. eds., John Wiley and Sons, New York (1987) and Friedmann (1989) *Science* 244:1275–1281. A tissue containing a recombinant nucleic acid molecule of the present invention may then be reintroduced into an animal using reconstitution techniques (See for example, Dick et al. (1985) *Cell* 42:71). The present invention also includes swine, preferably miniature swine, expressing in its cells a recombinant human class I gene. The recombinant constructs described above may be used to produce a transgenic pig by any method known in the art, including, but not limited to, microinjection, embryonic stem (ES) cell manipulation, electroporation, cell gun, transfection, transduction, retroviral infection, etc.

Transgenic swine of the present invention can be produced by introducing transgenes into the germline of the swine, particularly into the genome of bone marrow cells, e.g. hematopoietic cells. Embryonal target cells at various developmental stages can be used to introduce the human transgene construct. As is generally understood in the art, different methods are used to introduce the transgene depending on the stage of development of the embryonal target cell. One technique for transgenically altering a pig is to microinject a recombinant nucleic acid molecule into the male pronucleus of a fertilized egg so as to cause 1 or more copies of the recombinant nucleic acid molecule to be retained in the cells of the developing animal. The recombinant nucleic acid molecule of interest is isolated in a linear form with most of the sequences used for replication in bacteria removed. Linearization and removal of excess vector sequences results in a greater efficiency in production of transgenic mammals. See for example, Brinster et al. (1985) *PNAS* 82:44384442. In general, the zygote is the best target for micro-injection. In the swine, the male pronucleus reaches a size which allows reproducible injection of DNA solutions by standard microinjection techniques. Moreover, the use of zygotes as a target for gene transfer has a major advantage in that, in most cases, the injected DNA will be incorporated into the host genome before the first cleavage. Usually up to 40 percent of the animals developing from the injected eggs contain at least 1 copy of the recombinant nucleic acid molecule in their tissues. These transgenic animals will generally transmit the gene through the germ line to the next generation. The progeny of the transgenically manipulated embryos may be tested for the presence of the construct by Southern blot analysis of a segment of tissue. Typically, a small part of the tail is used for this purpose. The stable integration of the recombinant nucleic acid molecule into the genome of transgenic embryos allows permanent transgenic mammal lines carrying the recombinant nucleic acid molecule to be established.

Alternative methods for producing a mammal containing a recombinant nucleic acid molecule of the present invention include infection of fertilized eggs, embryo-derived stem cells, to potent embryonal carcinoma (EC) cells, or early cleavage embryos with viral expression vectors containing the recombinant nucleic acid molecule. (See for example, Palmiter et al. (1986) *Ann. Rev. Genet.* 20:465499 and Capecchi (1989) *Science* 244:1288–1292.)

Retroviral infection can also be used to introduce transgene into a swine. The developing embryo can be cultured in vitro to the blastocyst stage. During this time, the blastomeres can be targets for retroviral infection (Jaenich (1976) *PNAS* 73:1260–1264). Efficient infection of the blastomeres is obtained by enzymatic treatment to remove the zona pellucida (Hogan et al. (1986) in *Manipulating the Mouse Embryo*, Cold Spring Harbor Laboratory Press, Cold Spring Harbor, N.Y.). The viral vector system used to introduce the transgene is typically a replication-defective retrovirus carrying the transgene (Jahner et al. (1985) *PNAS* 82:6927–6931; Van der Putten et al. (1985) *PNAS* 82:6148–6152). Transfection can be obtained by culturing the blastomeres on a monolayer of virus-producing cells (Van der Putten, supra; Stewart et al. (1987) *EMBO J.* 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation typically occurs only in a subset of the cells which formed the transgenic swine. Further, the founder may contain various retroviral insertions of the transgene at different positions in the genome which generally will segregate in the offspring. In addition, it is also possible to introduce transgenes into the germ line, albeit with low efficiency, by intrauterine retroviral infection of the mid-gestation embryo (Jahner et al. (1982) supra).

A third approach, which may be useful in the construction of tansgenic swine, would target transgene introduction into an embryonal stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) *PNAS* 83:9065–9069; and Robertson et al. (1986) *Nature* 322:445448). Transgenes might be efficiently introduced into the ES cells by DNA transfection or by retrovirus-mediated transduction. Such transformed ES cells could thereafter be combined with blastocysts from a swine. The ES cells could be used thereafter to colonize the embryo and contribute to the germ line of the resulting chimeric pig. For review, see Jaenisch (1988) *Science* 240:1468–1474.

Introduction of the recombinant gene at the fertilized oocyte stage ensures that the gene sequence will be present in all of the germ cells and somatic cells of the transgenic "founder" swine. As used herein, founder (abbreviated "F") means the pig into which the recombinant gene was introduced at the one cell embryo stage. The presence of the recombinant gene sequence in the germ cells of the transgenic founder animal in turn means that approximately half of the founder animal's descendants will carry the activated recombinant gene sequence in all of their germ cells and somatic cells. Introduction of the recombinant gene sequence at a later embryonic stage might result in the gene's absence from some somatic cells of the founder animal, but the descendants of such an animal that inherit the gene will carry the activated recombinant gene in all of their germ cells and somatic cells.

Microinjection of Swine Oocytes

In preferred embodiments the transgenic swine of the present invention is produced by:

i) microinjecting a recombinant nucleic acid molecule into a fertilized swine egg to produce a genetically altered swine egg;

ii) implanting the genetically altered swine egg into a host female swine;

iii) maintaining the host female for a time period equal to a substantial portion of the gestation period of said swine fetus.

iv) harvesting a transgenic swine having at least one swine cell that has developed from the genetically altered mammalian egg, which expresses a human class I gene.

In general, the use of microinjection protocols in transgenic animal production is typically divided into four main phases: (a) preparation of the animals; (b) recovery and maintenance in vitro of one or two-celled embryos; (c) microinjection of the embryos and (d) reimplantation of embryos into recipient females. The methods used for producing transgenic livestock, particularly swine, do not differ in principle from those used to produce transgenic mice. Compare, for example, Gordon et al. (1983) *Methods in Enzymology* 101:411, and Gordon et al. (1980) *PNAS* 77:7380 concerning, generally, transgenic mice with Hammer et al. (1985) *Nature* 315:680, Hammer et al. (1986) *J Anim Sci* 63:269–278, Wall et al. (1985) *Biol Reprod.* 32:645–651, Pursel et al. (1989) *Science* 244:1281–1288, Vize et al. (1988) *J. Cell Science* 90:295–300, Muller et al. (1992) *Gene* 121:263–270, and Velander et al (1992) *PNAS* 89:12003–12007, each of which teach techniques for generating transgenic swine. See also, PCT Publication WO 90/03432, and PCT Publication WO 92/22646 and references cited therein.

One step of the preparatory phase comprises synchronizing the estrus cycle of at least the donor females, and inducing superovulation in the donor females prior to mating. Superovulation typically involves administering drugs at an appropriate stage of the estrus cycle to stimulate follicular development, followed by treatment with drugs to synchronize estrus and initiate ovulation. As described in the example below, pregnant mare's serum is typically used to mimic the follicle-stimulating hormone (FSH) in combination with human chorionic gonadotropin (hCG) to mimic luteinizing hormone (LH). The efficient induction of superovulation in swine depend, as is well known, on several variables including the age and weight of the females, and the dose and timing of the gonadotropin administration. See for example, Wall et al. (1985) *Biol. Reprod.* 32:645 describing superovulation of pigs. Superovulation increases the likelihood that a large number of healthy embryos will be available after mating, and further allows the practitioner to control the timing of experiments.

After mating, one or two-cell fertilized eggs from the superovulated females are harvested for microinjection. A variety of protocols useful in collecting eggs from pigs are known. For example, in one approach, oviducts of fertilized superovulated females can be surgically removed and isolated in a buffer solution/culture medium, and fertilized eggs expressed from the isolated oviductal tissues. See, Gordon et al. (1980) *PNAS* 77:7380; and Gordon et al. (1983) *Methods in Enzymology* 101:411. Alternatively, the oviducts can be cannulated and the fertilized eggs can be surgically collected from anesthetized animals by flushing with buffer solution/culture medium, thereby eliminating the need to sacrifice the animal. See Hammer et al. (1985) *Nature* 315:600. The timing of the embryo harvest after mating of the superovulated females can depend on the length of the fertilization process and the time required for adequate enlargement of the pronuclei. This temporal waiting period can range from, for example, up to 48 hours for larger breeds of swine. Fertilized eggs appropriate for microinjection, such as one-cell ova containing pronuclei, or two-cell embryos, can be readily identified under a dissecting microscope.

The equipment and reagents needed for microinjection of the isolated swine embryos are similar to that used for the mouse. See, for example, Gordon et al. (1983) *Methods in Enzymology* 101:411; and Gordon et al. (1980) *PNAS* 77:7380, describing equipment and reagents for microinjecting embryos. Briefly, fertilized eggs are positioned with an egg holder (fabricated from 1 mm glass tubing), which is attached to a micro-manipulator, which is in turn coordinated with a dissecting microscope optionally fitted with differential interference contrast optics. Where visualization of pronuclei is difficult because of optically dense cytoplasmic material, such as is generally the case with swine embryos, centrifugation of the embryos can be carried out without compromising embryo viability. Wall et al. (1985) *Biol. Reprod.* 32:645. Centrifugation will usually be necessary in this method. A recombinant nucleic acid molecule of the present invention is provided, typically in linearized form, by linearizing the recombinant nucleic acid molecule with at least 1 restriction endonuclease, with an end goal being removal of any prokaryotic sequences as well as any unnecessary flanking sequences. In addition, the recombinant nucleic acid molecule containing the tissue specific promoter and the human class I gene may be isolated from the vector sequences using 1 or more restriction endonucleases. Techniques for manipulating and linearizing recombinant nucleic acid molecules are well known and include the techniques described in *Molecular Cloning: A Laboratory Manual*, Second Edition. Maniatis et al. eds., Cold Spring Harbor, N.Y. (1989).

The linearized recombinant nucleic acid molecule may be microinjected into the swine egg to produce a genetically altered mammalian egg using well known techniques. Typically, the linearized nucleic acid molecule is microinjected directly into the pronuclei of the fertilized eggs as has been described by Gordon et al. (1980) *PNAS* 77:7380–7384. This leads to the stable chromosomal integration of the recombinant nucleic acid molecule in a significant population of the surviving embryos. See for example, Brinster et al. (1985) *PNAS* 82:4438–4442 and Hammer et al. (1985) *Nature* 315:600–603. The microneedles used for injection, like the egg holder, can also be pulled from glass tubing. The tip of a microneedle is allowed to fill with plasmid suspension by capillary action. By microscopic visualization, the microneedle is then inserted into the pronucleus of a cell held by the egg holder, and plasmid suspension injected into the pronucleus. If injection is successful, the pronucleus will generally swell noticeably. The microneedle is then withdrawn, and cells which survive the microinjection (e.g. those which do not lysed) are subsequently used for implantation in a host female.

The genetically altered mammalian embryo is then transferred to the oviduct or uterine horns of the recipient. Microinjected embryos are collected in the implantation pipette, the pipette inserted into the surgically exposed oviduct of a recipient female, and the microinjected eggs expelled into the oviduct. After withdrawal of the implantation pipette, any surgical incision can be closed, and the embryos allowed to continue gestation in the foster mother. See, for example, Gordon et al. (1983) *Methods in Enzymology* 101:411; Gordon et al. (1980) *PNAS* 77:7390; Hammer et al. (1985) *Nature* 315:600; and Wall et al. (1985) *Biol. Reprod.* 32:645.

The host female mammals containing the implanted genetically altered mammalian eggs are maintained for a sufficient time period to give birth to a transgenic mammal having at least 1 cell, e.g. a bone marrow cell, e.g. a hematopoietic cell, which expresses the recombinant nucleic acid molecule of the present invention that has developed from the genetically altered mammalian egg.

At two-four weeks of age (post-natal), tail sections are taken from the piglets and digested with Proteinase K. DNA from the samples is phenol-chloroform extracted, then digested with various restriction enzymes. The DNA digests are electrophoresed on a Tris-borate gel, blotted on nitrocellulose, and hybridized with a probe consisting of the at least a portion of the coding region of the recombinant cDNA of interest which had been labeled by extension of random hexamers. Under conditions of high stringency, this probe should not hybridize with the endogenous pig gene, and will allow the identification of transgenic pigs.

According to a preferred specific embodiment of the invention, a transgenic pig may be produced by the methods as set forth in Example 1.

EXAMPLE 1

PRODUCTION OF TRANSGENIC PIGS WHICH EXPRESS A HUMAN NUCLEIC ACID ENCODING A MHC CLASS I PROTEIN

Estrus is synchronized in sexually mature gilts (>7 months of age) by feeding an orally active progestogen (allyl trenbolone, AT: 15 mg/gilt/day) for 12 to 14 days. On the last day of AT feeding all gilts are given an intramuscular injection (IM) of prostaglandin $F_{2a}$ (Lutalyse: 10 mg/injection) at 0800 and 1600. Twenty-four hours after the last day of AT consumption all donor gilts are given a single IM injection of pregnant mare serum gonadotropin (PMSG: 1500 IU). Human chorionic gonadotropin (HCG: 750 IU) is administered to all donors at 80 hours after PMSG.

Following AT withdrawal, donor and recipient gilts are checked twice daily for signs of estrus using a mature boar. Donors which exhibited estrus within 36 hours following HCG administration are bred at 12 and 24 hours after the onset of estrus using artificial and natural (respectively) insemination.

Between 59 and 66 hours after the administration of HCG, one- and two-cell ova are surgically recovered from bred donors using the following procedure. General anesthesia is induced by administering 0.5 mg of acepromazin/kg of bodyweight and 1.3 mg ketamine/kg of bodyweight via a peripheral ear vein. Following anesthetization, the reproductive tract is exteriorized following a midventral laparotomy. A drawn glass cannula (O.D. 5 mm, length 8 cm) is inserted into the ostium of the oviduct and anchored to the infundibulum using a single silk (2–0) suture. Ova are flushed in retrograde fashion by inserting a 20 g needle into the lumen of the oviduct 2 cm anterior to the uterotubal junction. Sterile Dulbecco's phosphate buffered saline (PBS) supplemented with 0.4% bovine serum albumin (BSA) is infused into the oviduct and flushed toward the glass cannula. The medium is collected into sterile 17×100 mm polystyrene tubes. Flushings are transferred to 10×60 mm petri dishes and searched at lower power (50×). All one- and two-cell ova are washed twice in Brinster's Modified Ova Culture-3 medium (BMOC-3) supplemented with 1.5% BSA and transferred to 50 ml drops of BMOC-3 medium under oil. Ova are stored at 38° C. under a 90% $N_2$, 5% $O_2$, 5% $CO_2$ atmosphere until microinjection is performed.

One- and two-cell ova are placed in an Eppendorf tube (15 ova per tube) containing 1 ml HEPES Medium supplemented with 1.5% BSA and centrifuged for 6 minutes at 14000×g in order to visualize pronuclei in one-cell and nuclei in two-cell ova. Ova are then transferred to a 5–10 ml drop of HEPES medium under oil on a depression slide. Microinjection is performed using a Laborlux microscope with Nomarski optics and two Leitz micromanipulators. 10–1700 copies of a DNA construct which includes the human gene operably linked to a promoter (1 ng/ml of Tris-EDTA buffer) are injected into one pronuclei in one-cell ova or both nuclei in two-cell ova.

Microinjected ova are returned to microdrops of BMOC-3 medium under oil and maintained at 38° C. under a 90% $N_2$, 5% $CO_2$, 5% $O_2$ atmosphere prior to their transfer to suitable recipients. Ova are transferred within 10 hours of recovery.

Only recipients which exhibited estrus on the same day or 24 hours later than the donors are utilized for embryo transfer. Recipients are anesthetized as described above. Following exteriorization of one oviduct, at least 30 injected one and/or two-cell ova and 4–6 control ova are transferred in the following manner. The tubing from a 21 g×¾ butterfly infusion set is connected to a 1 cc syringe. The ova and one to two mls of BMOC-3 medium are aspirated into the tubing. The tubing is then fed through the ostium of the oviduct until the tip reached the lower third or isthmus of the oviduct. The ova are subsequently expelled as the tubing is slowly withdrawn.

The exposed portion of the reproductive tract is bathed in a sterile 10% glycerol/ 0.9% saline solution and returned to the body cavity. The connective tissue encompassing the linea alba, the fat and the skin are sutured as three separate layers. An uninterrupted Halstead stitch is used to close the lina alba. The fat and skin are closed using a simple continuous and mattress stitch, respectively. A topical antibacterial agent (Furazolidone) is then administered to the incision area.

Recipients are penned in groups of four and fed 1.8 kg of a standard 16% crude protein corn-soybean ration. Beginning on day 18 (day 0=onset of estrus), all recipients are checked daily for signs of estrus using a mature boar. On day 35, pregnancy detection is performed using ultrasound. On day 107 of gestation recipients are transferred to the farrowing suite. In order to ensure attendance at farrowing time, farrowing is induced by the administration of prostaglandin $F_{2\alpha}$, (10 mg/injection) at 0800 and 1400 hours on day 112 of gestation. Recipients should farrow within about 34 hours of $PGF_{2\alpha}$ administration.

Use of Transgenic Swine Hematopoietic Stem Cells in Xenogeneic Transplant

The following procedure was designed to lengthen the time an implanted swine organ (a xenograft) survives in a xenogeneic host prior to rejection. The organ can be any organ, e.g., a liver, e.g., a kidney, e.g., a heart. The main strategies are elimination of natural antibodies by perfusion, transplantation of tolerance-inducing transgenic swine stem cells, and optionally, the implantation of donor stromal tissue. One or both, of the donor stem cells, or some or all of the cells of the graft, express one or more human MHC class I proteins. Preparation of the recipient for transplantation includes any or all of these steps. Preferably they are carried out in the following sequence.

First, a preparation of horse anti-human thymocyte globulin (ATG) is intravenously injected into the recipient. The antibody preparation eliminates mature T cells and natural killer cells. Anti-human ATG obtained from any mammalian host can also be used, e.g., ATG produced in pigs, although thus far preparations of pig ATG have been of lower titer than horse-derived ATG. ATG is superior to anti-NK cell monoclonal Antibodies, as the latter are generally not lytic to all host NK cells, while the polyclonal mixture in ATG is capable of lysing all host NK cells. Anti-NK monoclonal antibodies can, however, be used.

The presence of donor antigen in the host thymus during the time when host T cells are regenerating post-transplant is critical for tolerizing host T cells. If donor hematopoietic stem cells are not able to become established in the host thymus and induce tolerance before host T cells regenerate repeated doses of anti-recipient T cell antibodies may be necessary throughout the non-myeloablative regimen. Continuous depletion of host T cells may be required for several weeks. Alternatively, e.g. if this approach is not successful, and tolerance (as measured by donor skin graft acceptance, specific cellular hyporesponsiveness in vitro, and humoral tolerance) is not induced in these animals, the approach can be modified to include host thymectomy. Immunocompetence can be measured by the ability to reject a non-donor type allogeneic donor skin graft, and to survive in a pathogen-containing environment.

It may also be necessary or desirable to splenectomize the recipient in order to avoid anemia.

Second, the recipient is administered low dose radiation in order to create hematopoietic space. A sublethal dose of between 100 rads and 400 rads whole body radiation, plus 700 rads of local thymic radiation, has been found effective for this purpose.

Third, natural antibodies are absorbed from the recipient's blood by hemoperfusion of a swine liver or absorption on an antigen column. Pre-formed natural antibodies (nAB) are the primary agents of graft rejection. Natural antibodies bind to xenogeneic endothelial cells and are primarily of the IgM class. These antibodies are independent of any known previous exposure to antigens of the xenogeneic donor. B cells that produce these natural antibodies tend to be T cell-independent, and are normally tolerized to self antigen by exposure to these antigens during development. The mechanism by which newly developing B cells are tolerized is unknown. The liver is a more effective absorber of natural antibodies than the kidney.

The fourth step in the non-myeloablative procedure is to implant donor stromal tissue, preferably obtained from fetal liver, thymus, and/or fetal spleen, into the recipient, preferably in the kidney capsule. Stem cell engraftment and hematopoiesis across disparate species barriers is enhanced by providing a hematopoietic stromal environment from the donor species. The stromal matrix supplies species-specific factors that are required for interactions between hematopoietic cells and their stromal environment, such as hematopoietic growth factors, adhesion molecules, and their ligands. It will generally be preferable to replace this step with the administration of swine cytokines.

The thymus is the major site of T cell maturation. Each organ includes an organ specific stromal matrix that can support differentiation of the respective undifferentiated stem cells implanted into the host. Although adult thymus may be used, fetal tissue obtained sufficiently early in gestation is preferred because it is free from mature T lymphocytes which can cause GVHD. Fetal tissues also tend to survive better than adult tissues when transplanted. As an added precaution against GVHD, thymic stromal tissue can be irradiated prior to transplantation, e.g., irradiated at 1000 rads. As an alternative or an adjunct to implantation, fetal liver cells can be administered in fluid suspension. (The use of transgenic "humanized" swine cells (which can more effectively compete with host stem cells to repopulate the host) may eliminate the need for this step.) Fifth, transgenic swine bone marrow stem cells (BMC), e.g., swine BMC engineered to express a human MHC class I protein, are injected into the recipient. Donor BMC home to appropriate sites of the recipient and grow contiguously with remaining host cells and proliferate, forming a chimeric lymphohematopoietic population. By this process, newly forming B cells (and the antibodies they produce) are exposed to donor antigens, so that the transplant will be recognized as self. Tolerance to the donor is also observed at the T cell level in animals in which hematopoietic stem cell, e.g., BMC, engraftment has been achieved. When an organ graft is placed in such a recipient several months after bone marrow chimerism has been induced, natural antibody against the donor will have disappeared, and the graft should be accepted by both the humoral and the cellular arms of the immune system. This approach has the added advantage of permitting organ transplantation to be performed sufficiently long following transplant of hematopoietic cells, e.g., BMT, e.g., a fetal liver suspension, that normal health and immunocompetence will have been restored at the time of organ transplantation. The use of xenogeneic donors allows the possibility of using bone marrow cells and organs from the same animal, or from genetically matched animals.

While any of these procedures may aid the survival of an implanted organ, best results are achieved when all steps are used in combination.

The donor of the implant and the individual that supplies either the tolerance-inducing hematopoietic cells or the liver to be perfused should be the same individual or should be as closely related as possible. For example, it is preferable to derive implant tissue from a colony of donors that is highly inbred.

Other Embodiments

Stromal tissue introduced prior to hematopoietic cell transplant, e.g., BMT, may be varied by: (1) administering the fetal liver and thymus tissue as a fluid cell suspension; (2) administering fetal liver or thymus stromal tissue but not both; (3) placing a stromal implant into other encapsulated, well-vascularized sites, or (4) using adult thymus or fetal spleen as a source of stromal tissue.

The methods of the invention are particularly useful for replacing a tissue or organ afflicted with a neoplastic disorder, particularly a disorder which is resistant to normal modes of therapy, e.g., chemotherapy or radiation therapy. In preferred embodiments: the graft includes tissue from the digestive tract or gut, e.g., tissue from the stomach, or bowel tissue, e.g., small intestine, large intestine, or colon; the graft replaces a portion of the recipient's digestive system e.g., all or part of any of the digestive tract or gut, e.g., the stomach, bowel, e.g., small intestine, large intestine, or colon.

Tolerance, as used herein, refers not only to complete immunologic tolerance to an antigen, but to partial immunologic tolerance, i.e., a degree of tolerance to an antigen which is greater than what would be seen if a method of the invention were not employed.

As is discussed herein, it is often desirable to expose a graft recipient to irradiation in order to promote the development of mixed chimerism. The inventor has discovered that it is possible to induce mixed chimerism with less radiation toxicity by fractionating the radiation dose, i.e., by delivering the radiation in two or more exposures or sessions. Accordingly, in any method of the invention calling for the irradiation of a recipient, e.g., a primate, e.g., a human, recipient, of a xenograft or allograft, the radiation can either be delivered in a single exposure, or more preferably, can be fractionated into two or more exposures or sessions. The sum of the fractionated dosages is preferably equal, e.g., in rads or Gy, to the radiation dosage which can result in mixed chimerism when given in a single exposure. The fractions are preferably approximately equal in dosage. For example, a single dose of 700 rads can be replaced with, e.g., two fractions of 350 rads, or seven fractions of 100 rads. Hyperfractionation of the radiation dose can also be used in methods of the invention. The fractions can be delivered on the same day, or can be separated by intervals of one, two, three, four, five, or more days. Whole body irradiation, thymic irradiation, or both, can be fractionated.

The inventor has also discovered that much or all of the preparative regimen can be delivered or administered to a recipient within a few days, preferably within 72, 48, or 24 hours, of transplantation of tolerizing stem cells and/or the graft. This is particularly useful in the case of humans receiving grafts from cadavers. Accordingly, in any of the methods of the invention calling for the administration of treatments prior to the transplant of stem cells and/or a graft, e.g., treatments to inactivate or deplete host antibodies, treatments to inactivate host T cells or NK cells, or irradiation, the treatment(s) can be administered, within a few days, preferably within 72, 48, or 24 hours, of transplantation of the stem cells and/or the graft. In particular, primate, e.g., human, recipients can be given any or all of treatments to inactivate or deplete host antibodies, treatments to inactivate host T cells or NK cells, or irradiation, within a few days, preferably within 72, 48, or 24 hours, of transplantation of stem cells and/or the graft. For example, treatment to deplete recipient T cells and/or NK cells, e.g., administration of ATG, can be given on day −2, −1, and 0, and WBI, thymic irradiation, and stem cell, e.g., bone marrow stem cells, administered on day 0. (The graft, e.g., a renal allograft, is transplanted on day 0).

Methods of the invention can include recipient splenectomy.

As is discussed herein, hemoperfusion, e.g., hemoperfusion with a donor organ, can be used to deplete the host of natural antibodies. Other methods for depleting or otherwise inactivating natural antibodies can be used with any of the methods described herein. For example, drugs which deplete or inactivate natural antibodies, e.g., deoxyspergualin (DSG) (Bristol), or anti-IgM antibodies, can be administered to the recipient of an allograft or a xenograft. One or more of, DSG (or similar drugs), anti-IgM antibodies, and hemoperfusion, can be used to deplete or otherwise inactivate recipient natural antibodies in methods of the invention. DSG at a concentration of 6 mg/kg/day, i.v., has been found useful in suppressing natural antibody function in pig to cynomolgus kidney transplants.

Some of the methods described herein use lethal irradiation to create hematopoietic space, and thereby prepare a recipient for the administration of allogeneic, xenogeneic, syngeneic, or genetically engineered autologous, stem cells. In any of the methods described herein, particularly primate or clinical methods, it is preferable to create hematopoietic space for the administration of such cells by non-lethal means, e.g., by administering sub-lethal doses of irradiation, bone marrow depleting drugs, or antibodies. The use of sublethal levels of bone marrow depletion allows the generation of mixed chimerism in the recipient. Mixed chimerism is generally preferable to total or lethal ablation of the recipient bone marrow followed by complete reconstitution of the recipient with administered stem cells.

Alternative methods for the inactivation of thymic T cells are also included in embodiments of the invention. Some of the methods described herein include the administration of thymic irradiation to inactivate host thymic-T cells or to otherwise diminish the host's thymic-T cell mediated responses to donor antigens. It has been discovered that the thymic irradiation called for in allogeneic or xenogeneic methods of the invention can be supplemented with, or replaced by, other treatments which diminish (e.g., by depleting thymic-T cells and/or down modulating one or more of the T cell receptor (TCR), CD4 co-receptor, or CD8 co-receptor) the host's thymic-T cell mediated response. For example, thymic irradiation can be supplemented with, or replaced by, anti-T cell antibodies (e.g., anti-CD4 and/or anti-CD8 monoclonal antibodies) administered a sufficient number of times, in sufficient dosage, for a sufficient period of time, to diminish the host's thymic-T cell mediated response.

For best results, anti-T cell antibodies should be administered repeatedly. E.g., anti-T cell antibodies can be administered one, two, three, or more times prior to donor bone marrow transplantation. Typically, a pre-bone marrow transplantation dose of antibodies will be given to the patient about 5 days prior to bone marrow transplantation. Additional, earlier doses 6, 7, or 8 days prior to bone marrow transplantation can also be given. It may be desirable to administer a first treatment then to repeat pre-bone marrow administrations every 1–5 days until the patient shows excess antibodies in the serum and about 99% depletion of peripheral T cells and then to perform the bone marrow transplantation. Anti-T cell antibodies can also be administered one, two, three, or more times after donor bone marrow transplantation. Typically, a post-bone marrow transplant treatment will be given about 2–14 days after bone marrow transplantation. The post bone marrow administration can be repeated as many times as needed. If more than one administration is given the administrations can be spaced about 1 week apart. Additional doses can be given if the patient appears to undergo early or unwanted T cell recovery. Preferably, anti-T cell antibodies are administered at least once (and preferably two, three, or more times) prior to donor bone marrow transplantation and at least once (and preferably two, three, or more times) after donor bone marrow transplantation.

Some of the methods herein include the administration of hematopoietic stem cells to a recipient. In many of those methods, hematopoietic stem cells are administered prior to or at the time of the implantation of a graft (an allograft or a xenograft), the primary purpose of the administration of hematopoietic stem cells being the induction of tolerance to the graft. The inventors have found that one or more subsequent administrations (e.g., a second, third, fourth, fifth, or further subsequent administration) of hematopoietic stem cells can be desirable in the creation and/or maintenance of tolerance. Thus, the invention also includes methods in which hematopoietic stem cells are administered to a recipient, e.g., a primate, e.g., a human, which has previously been administered hematopoietic stem cells as part of any of the methods referred to herein.

While not wishing to be bound by theory the inventor believes that repeated stem cell administration may promote chimerism and possibly long-term deletional tolerance in graft recipients. Accordingly, any method referred to herein which includes the administration of hematopoietic stem cells can further include multiple administrations of stem cells. In preferred embodiments: a first and a second administration of stem cells are provided prior to the implantation of a graft; a first administration of stem cells is provided prior to the implantation of a graft and a second administration of stem cells is provided at the time of implantation of the graft. In other preferred embodiments: a first administration of stem cells is provided prior to or at the time of implantation of a graft and a second administration of stem cells is provided subsequent to the implantation of a graft. The period between administrations of hematopoietic stem cells can be varied. In preferred embodiments a subsequent administration of hematopoietic stem cell is provided: at least two days, one week, one month, or six months after the previous administration of stem cells; at least two days, one week, one month, or six months after the implantation of the graft.

The method can further include the step of administering a second or subsequent dose of hematopoietic stem cells: when the recipient begins to show signs of rejection, e.g., as evidenced by a decline in function of the grafted organ, by a change in the host donor specific antibody response, or by a change in the host lymphocyte response to donor antigen; when the level of chimerism decreases; when the level of chimerism falls below a predetermined value; when the level of chimerism reaches or falls below a level where staining with a monoclonal antibody specific for a donor PBMC antigen is equal to or falls below staining with an isotype control which does not bind to PBMC's, e.g. when the donor specific monoclonal stains less than 1–2% of the cells; or generally, as is needed to maintain tolerance or otherwise prolong the acceptance of a graft. Thus, method of the invention can be modified to include a further step of determining if a subject which has received a one or more administrations of hematopoietic stem cells is in need of a subsequent administration of hematopoietic stem cells, and if so, administering a subsequent dose of hematopoietic stem cells to the recipient.

Any of the methods referred to herein can include the administration of agents, e.g., 15-deoxyspergualin, mycophenolate mofetil, brequinar sodium, or similar agents, which inhibit the production, levels, or activity of antibodies in the recipient. One or more of these agents can be administered: prior to the implantation of donor tissue, e.g., one, two, or three days, or one, two, or three weeks before implantation of donor tissue; at the time of implantation of donor tissue; or after implantation of donor tissue, e.g., one, two, or three days, or one, two or three weeks after, implantation of a graft.

The administration of the agent can be initiated: when the recipient begins to show signs of rejection, e.g., as evidenced by a decline in function of the grafted organ, by a change in the host donor specific antibody response, or by a change in the host lymphocyte response to donor antigen; when the level of chimerism decreases; when the level of chimerism falls below a predetermined value; when the level of chimerism reaches or falls below a level where staining with a monoclonal antibody specific for a donor PBMC antigen is equal to or falls below staining with an isotype control which does not bind to PBMC's, e.g. when the donor specific monoclonal stains less than 1–2% of the cells; or generally, as is needed to maintain tolerance or otherwise prolong the acceptance of a graft.

The period over which the agent is administered (or the period over which clinically effective levels are maintained in the subject) can be long term, e.g., for six months or more or a year or more, or short term, e.g., for less than a year, more preferably six months or less, more preferably one month or less, and more preferably two weeks or less. The period will generally be at least about one week and preferably at least about two weeks in duration. In preferred embodiments the period is two or three weeks long.

Preferred embodiments include administration of 15-deoxyspergualin (6 mg/kg/day) for about two weeks beginning on the day of graft implantation.

Some of the methods referred to herein include steps in which antibodies, e.g., preformed natural antibodies, are removed from the blood of a recipient. For example, in some methods antibodies are removed by hemoperfusion of an organ from the donor species. The inventor has discovered that an α1–3 galactose linkage epitope-affinity matrix, e.g., in the form of an affinity column, is useful for removing antibodies from the recipient's blood. Accordingly, the use of an α1–3 galactose linkage epitope-affinity matrix, e.g., matrix bound linear B type VI carbohydrate, can be added to any method referred to herein and can be used in addition to or in place of any antibody perfusion or removal technique, e.g., organ perfusion, in any method referred to herein.

Some of the methods referred to herein include the administration of hematopoietic stem cells to a recipient. In many of those methods hematopoietic stem cells are administered prior to or at the time of the administration of a graft (an allograft or a xenograft), the primary purpose of the administration of hematopoietic stem cells being the induction of tolerance to the graft. The inventors have found that administration of one or more cytokines, preferably a cytokine from the species from which the stem cells are derived, can promote tolerance or otherwise prolong acceptance of a graft. Thus, the invention also includes methods in a subject which has previously been administered donor hematopoietic stem cells, is administered one or more cytokine, e.g., a donor-species cytokine.

Although not wishing to be bound by theory, the inventor believes that the cytokines, particularly donor species cytokines, promote the engraftment and/or function of donor stem cells or their progeny cells. Accordingly, any method referred to herein which includes the administration of hematopoietic stem cells can further include the administration of a cytokine, e.g., SCF, IL-3, or GM-CSF. In preferred embodiments the cytokine one which is species specific in its interaction with target cells.

Administration of a cytokine can begin prior to, at, or after the implantation of a graft or the implantation of stem cells.

The method can further include the step of administering a first or subsequent dose of a cytokine to the recipient: when the recipient begins to show signs of rejection, e.g., as evidenced by a decline in function of the grafted organ, by a change in the host donor specific antibody response, or by a change in the host lymphocyte response to donor antigen; when the level of chimerism decreases; when the level of chimerism falls below a predetermined value; when the level of chimerism reaches or falls below a level where staining with a monoclonal antibody specific for a donor PBMC antigen is equal to or falls below staining with an isotype control which does not bind to PBMC's, e.g. when the donor specific monoclonal stains less than 1–2% of the cells; or generally, as is needed to maintain tolerance or otherwise prolong the acceptance of a graft. Thus, method of the invention can be modified to include a further step of determining if a subject is in need of cytokine therapy and if so, administering a cytokine.

The period over which the cytokine(s) is administered (or the period over which clinically effective levels are maintained in the subject) can be long term, e.g., , for six months of more or a year or more, or short term, e.g., for a year or less, more preferably six months or less, more preferably one month or less, and more preferably two weeks or less.

The period will generally be at least about one week and preferably at least about two weeks in duration.

In preferred embodiments the recipient is a primate, e.g., a human, and the donor is from a different species, e.g., the donor is a pig and: pig SCF is administered; pig IL-3 is administered; a combination of pig SCF and pig IL-3 is administered; a pig specific hematopoiesis enhancing factor, e.g., pig GM-SCF, is administered, e.g., after the implantation of stem cells, e.g., about a month after the implantation of stem cells.

A particularly preferred embodiment combines a short course, e.g., about a month, of cyclosporine or a similar agent, a short course, e.g., about two weeks, of 15-deoxyspergualin or a similar agent, and a short course, e.g., about two weeks, of donor specific cytokines, e.g., SCF and IL-3. In Cynomolgus monkeys receiving pig grafts and pig stem cells, treatment which included the combination of cyclosporine (15mg/kg/day for 28 days), 15-deoxyspergualin (6 mg/kg/day for two weeks), and recombinant pig cytokines (SCF and IL-3, each at 10 μg/kg/day, i.v., for two weeks) was found to be useful. Administration began at the time of graft implant. (The monkeys were also given a preparative regime consisting of 3×100 cGy total body irradiation on day −6, and −5 and hemoperfusion with a pig liver just prior to stem cell administration.)

An anti-CD2 antibody, preferably a monoclonal, e.g., BTI-322, or a monoclonal directed at a similar or overlapping epitope, can be used in addition to or in place of any anti-T cell antibodies (e.g., ATG) in any method referred to herein.

The suitability of a particular class I protein for protecting for protecting a target cell from NK cell killing can be evaluated in vitro, e.g., with in vitro killing experiments. This approach can be used to evaluate the extent to which a given class I protein can protect a target cell from a spectrum of NK receptors. This approach can also be used to assay chimeric class I proteins for the ability to protect cells from attack by NK cells, e.g., NK cells having various NK receptors.

In methods of the invention, a human class I transgenic pig can be used as the bone marrow donor and a congenic pig without the human class I gene as the organ donor.

Naturally occurring HLA genes can be used in methods of the invention. However, DNA which encodes analogs of naturally HLA antigens can also be used. Analogs can differ from naturally occurring proteins in amino acid sequence or in ways that do not involve sequence, or both. Non-sequence modifications include in vivo or in vitro chemical derivatization. Non-sequence modifications include changes in acetylation, methylation, phosphorylation, carboxylation, or glycosylation.

Preferred analogs include nucleic acids which encode HLA A, B, C, or G antigens (or biologically active fragments thereof) whose sequences differ from the wild-type sequence by one or more conservative amino acid substitutions or by one or more non-conservative amino acid substitutions, deletions, or insertions which do not abolish the biological activity, i.e., the ability to protect against NK cell mediated attack. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative substitutions can be taken from the table below.

TABLE 1

CONSERVATIVE AMINO ACID REPLACEMENTS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

A fragment or analog can be tested for activity by determining if it can inhibit NK cell mediated attack of target cells. It may be desirable to first screen candidates for the ability to bind to an KIR and to then screen for the ability to inhibit NK cell mediated attack of target cells.

Analogs and fragments can be generated by methods known to those skilled in the art, e.g., those described below.

Fragments of a protein can be produced in several ways, e.g., recombinantly. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNA's which encode an array of fragments. DNA's which encode fragments of a protein can also be generated by random shearing, restriction digestion or a combination of the above-discussed methods.

Amino acid sequence variants of a protein can be prepared by random mutagenesis of DNA which encodes a protein or a particular domain or region of a protein. Useful methods include PCR mutagenesis and saturation mutagenesis. A library of random amino acid sequence variants can also be generated by the synthesis of a set of degenerate oligonucleotide sequences. (Methods for screening proteins in a library of variants are elsewhere herein.)

In PCR mutagenesis, reduced Taq polymerase fidelity is used to introduce random mutations into a cloned fragment of DNA (Leung et al., 1989, Technique 1:11–15). This is a very powerful and relatively rapid method of introducing random mutations. The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation mutagenesis allows for the rapid introduction of a large number of single base substitutions into cloned DNA fragments (Mayers et al., 1985, Science 229:242). This technique includes generation of mutations, e.g., by chemical treatment or irradiation of single-stranded DNA in vitro, and synthesis of a complimentary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, SA (1983) Tetrahedron 39:3; Itakura et al. (1981) Recombinant DNA, Proc 3rd Cleveland Sympos. Macromolecules, ed. AG Walton, Amsterdam: Elsevier pp273–289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386–390; Roberts et al. (1992) PNAS 89:2429–2433; Devlin et al. (1990) Science 249: 404–406; Cwirla et al. (1990) PNAS 87: 6378–6382; as well as U.S. Pat. Nos. 5,223,409, 5,198,346, and 5,096,815).

Non-random or directed, mutagenesis techniques can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1–3.

Alanine scanning mutagenesis is a useful method for identification of certain residues or regions of the desired protein that are preferred locations or domains for mutagenesis, Cunningham and Wells (*Science* 244:1081–1085, 1989). In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-mediated mutagenesis is a useful method for preparing substitution, deletion, and insertion variants of DNA, see, e.g., Adelman et al., (*DNA* 2:183, 1983). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci. USA*, 75: 5765[1978]).

Another method for preparing variants, cassette mutagenesis, is based on the technique described by Wells et al. (*Gene*, 34:315[1985]). The starting material is a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial mutagenesis can also be used to generate mutants. E.g., the amino acid sequences for a group of homologs or other related proteins are aligned, preferably to promote the highest homology possible. All of the amino acids which appear at a given position of the aligned sequences can be selected to create a degenerate set of combinatorial sequences. The variegated library of variants is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Various techniques are known in the art for screening generated mutant gene products. Techniques for screening large gene libraries often include cloning the gene library into replicable expression vectors, transforming appropriate cells with the resulting library of vectors, and expressing the genes under conditions in which detection of a desired activity, e.g., in this case, binding to a KIR. Each of the techniques described below is amenable to high through-put analysis for screening large numbers of sequences created, e.g., by random mutagenesis techniques.

Two hybrid assays can be used to identify fragments or analogs of a polypeptide which binds to a KIR. (The KIR is used as the bait protein and the library of variants of the HLA is expressed as fish fusion proteins.)

In one approach to screening assays, the candidate peptides are displayed on the surface of a cell or viral particle, and the ability of particular cells or viral particles to bind an appropriate receptor protein via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. (1991) *Bio/Technology* 9:1370–1371; and Goward et al. (1992) *TIBS* 18:136–140). In a similar fashion, a detectably labeled ligand can be used to score for potentially functional peptide homologs. Fluorescently labeled ligands, e.g., receptors, can be used to detect homolog which retain ligand-binding activity. The use of fluorescently labeled ligands, allows cells to be visually inspected and separated under a fluorescence microscope, or, where the morphology of the cell permits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical *E. coli* filamentous phages M13, fd., and fl are most often used in phage display libraries. Either of the phage gIII or gVIII coat proteins can be used to generate fusion proteins without disrupting the ultimate packaging of the viral particle. Foreign epitopes can be expressed at the $NH_2$-terminal end of pIII and phage bearing such epitopes recovered from a large excess of phage lacking this epitope (Ladner et al. PCT publication WO 90/02909; Garrard et al., PCT publication WO 92/09690; Marks et al. (1992) *J. Biol. Chem.* 267:16007–16010; Griffiths et al. (1993) *EMBO J* 12:725–734; Clackson et al. (1991) *Nature* 352:624–628; and Barbas et al. (1992) *PNAS* 89:44574461).

A common approach uses the maltose receptor of *E. coli* (the outer membrane protein, LamB) as a peptide fusion partner (Charbit et al. (1986) *EMBO* 5, 3029–3037). Oligonucleotides have been inserted into plasmids encoding the LamB gene to produce peptides fused into one of the extracellular loops of the protein. These peptides are available for binding to ligands, e.g., to antibodies, and can elicit an immune response when the cells are administered to animals. Other cell surface proteins, e.g., OmpA (Schorr et al. (1991) *Vaccines* 91, pp. 387–392), PhoE (Agterberg, et al. (1990) *Gene* 88, 37–45), and PAL (Fuchs et al. (1991) *Bio/Tech* 9, 1369–1372), as well as large bacterial surface structures have served as vehicles for peptide display. Peptides can be fused to pilin, a protein which polymerizes to form the pilus-a conduit for interbacterial exchange of genetic information (Thiry et al. (1989) *Appl. Environ. Microbiol.* 55, 984–993). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of may peptides copies on the host cells (Kuwajima et al. (1988) *Bio/Tech.* 6, 1080–1083). Surface proteins of other bacterial species have also served as peptide fusion partners. Examples include the Staphylococcus protein A and the outer membrane protease IgA of Neisseria (Hansson et al. (1992) *J. Bacteriol.* 174, 4239–4245 and Klauser et al. (1990) *EMBO J.* 9, 1991–1999).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein LacI to form a link between peptide and DNA (Cull et al. (1992) *PNAS USA* 89:1865–1869). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al. (1992) *Proc. Natl. Acad. Sci. U.S.A.* 89–1869)

This scheme, sometimes referred to as peptides-on-plasmids, differs in two important ways from the phage display methods. First, the peptides are attached to the C-terminus of the fusion protein, resulting in the display of the library members as peptides having free carboxy termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla, et al. (1990) *Proc. Natl. Acad Sci. U.S.A.* 87, 6378–6382) A second difference is the set of biological biases affecting the population of peptides actually present in the libraries. The LacI fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the LacI and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are underrepresented in the libraries (Gallop et al. (1994) *J. Med Chem.* 37(9):1233–1251). These particular biases are not a factor in the LacI display system.

The number of small peptides available in recombinant random libraries is enormous. Libraries of $10^7$–$10^9$ independent clones are routinely prepared. Libraries as large as $10^{11}$ recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3–6 orders of magnitude larger than the currently available phage/phagemid or plasmid libraries. Furthermore, the construction of the libraries, expression of the peptides, and screening, is done in an entirely cell-free format.

In one application of this method (Gallop et al. (1994) *J. Med. Chem.* 37(9):1233–1251), a molecular DNA library encoding $10^{12}$ decapeptides was constructed and the library expressed in an *E. coli* S30 in vitro coupled transcription/translation system. Conditions were chosen to stall the ribosomes on the mRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret, et al. (1992) *Anal. Biochem* 204,357–364). To identify the sequences of the active peptides one sequences the DNA produced by the phagemid host.

The high through-put assays described above can be followed by secondary screens to determine if a polypeptide can protect from NK cell mediated attack.

The antigen expressed by the MHC class I gene used in methods of the invention can differ in sequence from naturally occuring MHC class I genes. Preferrably the antigen has an amino acid sequence at least 60%, 80%, 90%, 95%, 98%, or 99% homologous to an amino acid sequence from a naturally occuring MHC class I gene.

In a preferred embodiment, the antigen expressed by the MHC class I gene used in methods of the invention differs in amino acid sequence at up to 1, 2, 3, 5, 10, 15, or 20 residues, from a naturally occuring MHC class I gene.

Other embodiments are within the following claims.

What is claimed is:

1. A method of inducing a least partial NK mediated immunologic tolerance in a recipient human to a graft obtained from a donor swine, the method comprising:

introducing into the recipient human a swine hematopoietic stem cell, wherein the cell comprises a transgene encoding a human MHC class I protein from a reactivity group of one or more alleles expressed by the recipient; and implanting the swine graft into the recipient human, wherein at least some of the cells of the swine graft express the human MHC class I protein, and wherein the implanting step is after or simultaneous with the introducing step;

wherein the introduction of said swine hematopoietic stem cells into the recipient human results in at least partial NK mediated immunologic tolerance to said swine graft.

2. The method of claim 1, wherein the human MHC class I protein is selected from the group consisting of HLA A, HLA B, HLA C, and HLA G.

3. The method of claim 2, wherein the human HLA C protein is a member of Reactivity Group I.

4. The method of claim 2, wherein the human HLA C protein is a member of Reactivity Group II.

5. The method of claim 1, wherein the cell includes a second transgene which encodes a second human MHC class I protein.

6. The method of claim 5, wherein the transgene encodes a Reactivity Group I HLA C protein and the second transgene encodes a Reactivity Group II HLA C protein.

7. The method of claim 1, wherein the MHC class I antigen is a chimeric HLA C class I protein.

8. The method of claim 7, wherein the transgene includes a first portion derived from a first allele of the gene encoding the HLA class I protein and a second portion derived from a second allele of the gene encoding the HLA class I protein.

9. The method of claim 1, wherein the MHC class I protein is an HLA C antigen comprising a serine at position 77 and a lysine at position 80.

10. The method of claim 1, wherein the cell is selected from the group consisting of a cord blood hematopoietic stem cell, a bone marrow hematopoietic stem cell, a fetal liver hematopoietic stem cell, a neonatal liver hematopoietic stem cell, a fetal spleen hematopoietic stem cell and a neonatal spleen hematopoietic stem cell.

11. The method of claim 1, wherein the cell is obtained from erythroid cells.

12. The method of claim 1, wherein the cell is obtained from myeloid cells.

13. The method of claim 1, wherein the cell is obtained from cultured cells.

14. The method of claim 1, wherein the cell is obtained from a transgenic swine.

15. The method of claim 1, wherein the cell and the graft are obtained from the same swine.

16. The method of claim 1, wherein the cell is obtained from a first swine and the graft is obtained from a second swine, wherein the first swine and the second swine are syngeneic.

* * * * *

UNITED STATES PATENT AND TRADEMARK OFFICE
CERTIFICATE OF CORRECTION

PATENT NO. : 6,558,663 B1
DATED : May 6, 2003
INVENTOR(S) : Joerg Seebach et al.

It is certified that error appears in the above-identified patent and that said Letters Patent is hereby corrected as shown below:

<u>Title page,</u>
Item [56], References Cited, U.S. PATENT DOCUMENTS, reference "6,030,838" replace "2/2000" with -- 3/1997 --
Item [57], ABSTRACT,
Line 3, after "disclosed" insert -- . --

Signed and Sealed this

Twenty-fourth Day of February, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,558,663 B1
DATED : May 6, 2003
INVENTOR(S) : Joerg Seebach et al.

It is certified that error appears in the above-identified patent and that said Letters Patent is hereby corrected as shown below:

<u>Title page,</u>
Item [56], References Cited, OTHER PUBLICATIONS, "Katz et al.," reference delete "144" and replace with -- 244 --

Signed and Sealed this

Twenty-seventh Day of April, 2004

JON W. DUDAS
*Acting Director of the United States Patent and Trademark Office*